United States Patent
Zhou

(10) Patent No.: US 12,274,686 B2
(45) Date of Patent: Apr. 15, 2025

(54) SPECIALIZED PRO-RESOLVING MEDIATORS (SPMs) AS MELANOCYTE GROWTH PROMOTER AND PRO-SURVIVAL FACTORS AND USES THEREOF

(71) Applicant: THE UNIVERSITY OF BRITISH COLUMBIA, Vancouver (CA)

(72) Inventor: Youwen Zhou, Vancouver (CA)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 18/026,765

(22) PCT Filed: Mar. 18, 2022

(86) PCT No.: PCT/CA2022/050415
§ 371 (c)(1),
(2) Date: Mar. 16, 2023

(87) PCT Pub. No.: WO2022/193029
PCT Pub. Date: Sep. 22, 2022

(65) Prior Publication Data
US 2023/0285344 A1     Sep. 14, 2023

Related U.S. Application Data

(60) Provisional application No. 63/163,241, filed on Mar. 19, 2021.

(51) Int. Cl.
*A61K 31/202* (2006.01)
*A61K 9/00* (2006.01)
*A61P 17/00* (2006.01)

(52) U.S. Cl.
CPC .......... *A61K 31/202* (2013.01); *A61K 9/0014* (2013.01); *A61K 9/0019* (2013.01); *A61P 17/00* (2018.01)

(58) Field of Classification Search
CPC .............................. A61K 31/202; A61P 17/00
See application file for complete search history.

(56) References Cited

U.S. PATENT DOCUMENTS

2017/0360073 A1   12/2017   Vadakkemuri

FOREIGN PATENT DOCUMENTS

| KR | 101900066 | 8/2018 |
|---|---|---|
| WO | 2016/144569 | 9/2016 |

(Continued)

OTHER PUBLICATIONS

Cezar et al.; "Treatment with maresin 1, a docosahexaenoic acid-derived pro-resolution lipid, protects skin from inflammation and oxidative stress caused by UVB irradiation"; 2019; nature /scientificreports; 9;3062, pp. 1-14; https://doi.org/10.1038/s41598-019-39584-6 (Year: 2019).*

(Continued)

*Primary Examiner* — Timothy P Thomas
(74) *Attorney, Agent, or Firm* — Bozicevic, Field & Francis LLP; Shweta Chandra

(57) ABSTRACT

This invention provides the use of specialized pro-resolving mediators (SPMs) for use as melanocyte growth promoters and pro-survival factors. More particularly, the SPM compositions are suitable for promoting melanocyte growth and/or survival to prevent depigmentation of melanocytes and/or promoting repigmentation in non-inflammatory depigmentation of melanocytes. Furthermore, the compositions may be used to treat dormant vitiligo lesions, chemically induced vitiligo, vitiligo that is non-responsive to inflammatory therapies, or canities.

13 Claims, 12 Drawing Sheets

(56) References Cited

FOREIGN PATENT DOCUMENTS

| WO | WO 2016/168574 | 10/2016 |
|---|---|---|
| WO | 2018/048358 | 3/2018 |
| WO | WO 2020/132161 | 6/2020 |

OTHER PUBLICATIONS

Prospera Biotech; "How does skin protect from ultraviolet radiation?" 2020; https://www.prosperabiotech.com/en/2020/04/06/how-does-skin-protect-from-ultraviolet-radiation/; accessed Sep. 19, 2023 (Year: 2020).*

Singh et al.; "The Role of IL-17 in vitiligo: A review"; 2016; Autoimmunity Reviews; 15:397-404 (Year: 2016).*

Saito-Sasaki et al.; "Maresin-1 suppresses imiquimod-induced skin inflammation by regulating IL-23 receptor expression"; 2018; Scientific Reports; 8:5522, pp. 1-8; DOI:10.1038/s41598-018-23623-9 (Year: 2018).*

Sahni et al.; "Stability in Vitiligo: Is there a Perfect Way to Predict it?"; 2013; J. Cutan. Aesthet. Surg.; 6(2): 75-82; doi: 10.4103/0974-2077.112667 (Year: 2013).*

Menon et al., (2017) "Pro-Resolution Potency of Resolvins D1, D2 and E1 on Neutrophil Migration and in Dermal Wound Healing", Nano Life, 7(1):1.20.

Albuquerque-Souza et al., (2020) "Maresin-1 and Resolvin E1 Promote Regenerative Properties of Periodontal Ligament Stem Cells Under Inflammatory Conditions", Frontiers in Immunology, 11:1-15.

Arnardottir et. al., (2014) "Aging delays resolution of acute inflammation in mice: reprogramming the host response with novel nanoproresolving medicines[1]", J Immunol, 193(8): 4235-4244.

Dalli et. al., (2016) "Maresin conjugates in tissue regeneration biosynthesis enzymes in human macrophages", PNAS, 113(43):12232-12237.

Fan et. al., (2018) "Retinoic Acid Receptor-Related Orphan Receptors: Critical Roles in Tumorigenesis", Fronteirs in Immunology, 9:1-10.

Gao et. al., (2018) "Pro-resolving mediator maresin 1 ameliorates pain hypersensitivity in a rat spinal nerve ligation model of neuropathic pain", Journal of Pain Research, 2018(11):1511-1519.

Han et. al., (2019) "A maresin 1/RORα/12-lipoxygenase autoregulatory circuit prevents inflammation and progression of nonalcoholic steatohepatitis", Journal of Clinical Investigation, 129(4):1684-1698.

Harris et. al., (2018) "A direct link between MITF, innate immunity, and hair graying", PLOS Biology, 1-27.

Hendaoui et. al., (2014) "Tenascin-C is required for normal Wnt/β-catenin signaling in the whisker follicle stem cell niche", Matrix Biology, 40:46-53.

Hwang et. al., (2019) "The Role of Maresins in Inflammatory Pain: Function of Macrophages in Wound Regeneration", International Journal of Molecular Sciences, 20(5849):1-16.

Li et. al., (2020) "Maresins: anti-inflammatory pro-resolving mediators with therapeutic potential", Eur Rev Med and Pharmacol Sci, 24:7442-7453.

Markworth et. al., (2021) "Metabolipidomic profiling reveals an age-related deficiency of skeletal muscle pro-resolving mediators that contributes to maladaptive tissue remodeling", Aging Cell, 20(e13393):1-16.

Randall et. al., (2008) "Stem cell factor/c-Kit signalling in normal and androgenetic alopecia hair follicles", Journal of Endocrinology, 197:11-23.

Seiberg, (2013) "Age-induced hair greying—the multiple effects of oxidative stress", International Journal of Cosmetic Science, 35:532-538.

Serhan et. al., (2009) "Maresins: novel macrophage mediators with potent antiinflammatory and proresolving actions", J. Exp. Med., 206(1):15-23.

Serhan et. al., (2012) "Macrophage proresolving mediator maresin 1 stimulates tissue regeneration and controls pain", FASEB J., 26(4):1755-1765.

Spite et. al., (2014) "Resolvins, Specialized Pro-Resolving Lipid Mediators and their Potential Roles in Metabolic Diseases", Cell Metab., 19(1):21-36.

Wang et. al., (2020) "Maresin 1 Promotes Wound Healing and Socket Bone Regeneration for Alveolar Ridge Preservation", Research Reports: Biological, 99(8):930-937.

Yang et. al., (2021) "Vitiligo Skin Biomarkers Associated With Favorable Therapeutic Response", Frontiers in Immunology, 12:1-12.

You et. al., (2013) "Priming of Autoreactive $CD8^T$ Cells Is Inhibited by Immunogenic Peptides Which Are Competitive for Major Histocompatibility Complex Class I Binding", Immune Network, 13(3):86-93.

You et. al., (2013) "Melanocyte-specific CD8+ T cells are associated with epidermal depigmentation in a novel mouse model of vitiligo", Clinical & Experimental Immunology, 174:38-44.

Zhang et. al., (2017) "Wnt/ β-catenin signaling promotes aging-associated hair graying in mice", Oncotarget, 8(41):69316-69327.

Zhou et. al., (2013) "Dermal Mesenchymal Stem Cells (DMSCs) Inhibit Skin-Homing CD8+ T Cell Activity, a Determining Factor of Vitiligo Patients' Autologous Melanocytes Transplantation Efficiency", PLOS ONE, 8(4):1-10.

Bara et al., (2015) "High content and high throughput screening to assess the angiogenic and neurogenic actions of mesenchymal stem cells in vitro", Experimental Cell Research, 333(1):93-104.

Chiang and Serhan (2020) "Specialized pro-resolving mediator network: an update on production and actions", 64 (3):443-462.

Matsumura et. al., (2016) "Hair follicle aging is driven by transepidermal elimination of stem cells via COL17A1 proteolysis", Stem Cells, 351(6273):575-589.

Osio et. al., (2013) "Role of macrophage infiltration in successful repigmentation in a new periphery-spreading vitiligo lesion in a male Japanese patient", Journal of Dermatology, 40:915-918.

Pyo et al., (2019) "Keratinocyte-derived IL-36γ plays a role in hydroquinone-induced chemical leukoderma through inhibition of melanogenesis in human epidermal melanocytes", Archives of Toxicology, 93:2307-2320.

Qiu et al., (2015) "SCF/c-kit signaling is required in 12-O-tetradecanoylphorbol-13-acetate-induced migration and differentiation of hair follicle melanocytes for epidermal pigmentation", Cell Tissue Res, 360(2):333-346.

Yamada et al., (2019) "CXCL12 regulates differentiation of human immature melanocyte precursors as well as their migration", Archives of Dermatological Research, 311(1):55-62.

Belpaire et al., (2022) "From IL-17 to IFN-γ in inflammatory skin disorders: Is transdifferentiation a potential treatment target?." Frontiers In immunology, vol. 13: 932265.

Marasca et al., (2021) "Onset of vitiligo in a psoriasis patient on ixekizumab." Dermatologic Therapy, vol. 34, No. 5: e15102.

Migayron et al. (2020) "Vitiligo, from physiopathology to emerging treatments: a review." Dermatology and Therapy, vol. 10, pp. 1185-1198.

Speeckaert et al., (2019) "Reinhart, Sofie Mylle, and Nanja van Geel. IL-17A is not a treatment target in progressive vitiligo." Pigment Cell & Melanoma Research, vol. 32, No. 6, pp. 842-847.

Extended European Search Report, Jan. 2, 2025, application No. 22770150, 1-4.

Su et. al., (2022) "LB1002 Melanocyte depletion in vitilgo and canities is associated with M2 macrophage deficiency and responds to modulation by M2-secreted soluble mediator maresin 1 in vitro and in vivo", Journal of Investigative Dermatology, 142(8):B30, XP093233603.

* cited by examiner

A

B

C

D

E

F

SPECIALIZED PRO-RESOLVING MEDIATORS (SPMs) AS MELANOCYTE GROWTH PROMOTER AND PRO-SURVIVAL FACTORS AND USES THEREOF

CROSS REFERENCE TO RELATED APPLICATION

This application claims the benefit of U.S. Provisional Patent Application Ser. No. 63/163,241 filed on 19 Mar. 2021, entitled "NOVEL USES OF A NATURAL COMPOUND AS A GROWTH PROMOTER AND PRO-SURVIVAL FACTOR OF MELANOCYTES".

FIELD OF THE INVENTION

This invention relates to the use of specialized pro-resolving mediators (SPMs) for use as melanocyte growth promoters and pro-survival factors. More particularly, the invention relates to SPM compositions that are for promoting melanocyte growth and/or survival to prevent depigmentation of melanocytes and/or promoting re-pigmentation in non-inflammatory depigmentation of melanocytes. Furthermore, the compositions may be used to treat dormant vitiligo lesions, chemically induced vitiligo, vitiligo that is non-responsive to inflammatory therapies, or canities.

BACKGROUND OF THE INVENTION

Physiological melanin pigmentation of post-embryonic skin and hair is maintained by melanocytes that are derived from differentiation and migration of melanocytes from the melanocyte stem cells (McSC) residing in the bulge region of the hair follicles. Adequate production and physiological distribution of pigmentation of the hair and skin are important not only for protection from harmful effects of ultraviolet light, but also for the psychosocial wellbeing of an individual. Melanin production can be lost due to melanocyte depletion, which occurs in a number of conditions, including vitiligo and canities.

Affecting 0.5%-2% of world's population, vitiligo[1] results in development of white patches of skin or hair or both resulting in highly visible and disfiguring appearances of the affected individuals, and can cause significant reduction of quality of life[2-5]. Although multiple pathogenic mechanisms have been proposed for vitiligo[6-10], melanocyte-specific autoimmune activation has the strongest experimental support. Specifically, immune active cytotoxic cells such as CD8+ T cells and memory T cells and[11-13] and NK cells[14] have been found in the skin lesions. Repigmentation can occur with immune suppressive treatments such as narrow band ultraviolet B phototherapy (NBUVB), topical calcineurin inhibitors, and topical or systemic steroids[15-22] [23]. Emerging and experimental therapies for vitiligo, such as JAK inhibitors[24] and IL15 inhibitors[25], also target various aspects of immune cytotoxicity against the melanocytes. These observations strongly support a pathogenic role of immune mediated melanocyte cytotoxicity in the development of vitiligo.

However, many aspects of vitiligo's clinical presentations cannot be fully explained solely by autoimmune/auto-inflammatory events: First, in most of vitiligo skin lesions, there are no typical signs of acute immune or inflammatory responses, such as erythema, tissue induration, elevated temperature or scale development, unlike other typical immune-mediated skin diseases such as eczema, a common Th2-mediated skin disease. Second, in a significant proportion of patients, especially those with vitiligo patches on the hands and feet, there is little response to treatments even with the strongest immune suppressants. Even in those who respond to immune suppressive treatments, the repigmentation is very slow (often taking 3-6 months) and mostly partial. In contrast, classic immune-mediated skin disease such as eczema respond much more rapidly (often in a few days or a few weeks) and completely to treatment with immune suppressants. These results suggest that there are additional factors present in the skin microenvironment that contribute to the depletion of melanocytes and preventing them from returning to vitiligo skin lesions. However, the definitive evidence of this has not been available.

In contrast to the patchy distribution of depigmentation in skin and hair in vitiligo, the depigmentation in canities (spontaneous aging associated greying of hair and skin) is much more diffused, with the depigmented hairs mixed with and dispersed among hairs with normal melanin pigmentation. Canities affects almost everyone in advanced age. Although not usually associated with major somatic symptoms, canities can result in significant psychosocial distress, especially in individuals with premature canities (development of white hair before age of 30). The exact mechanism leading to melanocyte depletion in canities is unknown. However, conclusive recent studies by Bing Zhang and colleagues using mouse models showed that melanocyte depletion in canities was not the result of immune response involving T and B lymphocytes. Instead it is the result of immune-independent exhaustion of melanocyte stem cells or precursor cells as a result of aging or hyper-activation of the sympathetic nervous system[26] [27].

The relationship between vitiligo and canities has been a subject of debate. Emerging reports suggest that these two conditions may be pathogenically related. First, J Smith reported that a child with vitiligo developed premature and diffused hair greying on the scalp that was different from the typical patchy distribution of vitiligo[28]. Second, in a large epidemiological analysis of 717 vitiligo patients, K Ezzedine et al. showed that 32.8% of vitiligo patients had premature canities, and this was increased to 46% in patients with pre-pubertal onset of vitiligo[29, 30]. Further, pre-pubertal onset vitiligo was strongly associated with an increased familial history of premature canities in family members without vitiligo[30]. Finally, mental stress has been shown to be strongly associated with development of both canities[26] [27] and vitiligo.[29, 30] [31] However, there have been no unifying pathogenic mechanisms linking vitiligo with canities.

Macrophages play important roles in the development of skin diseases, especially in inflammation, wound healing and neoplasia. M1 macrophages promote inflammation while the alternatively activated M2 macrophages are involved in resolution of the immune or inflammatory responses and in tissue repair. In addition, we and others have found increased M2-like macrophages in malignant conditions such as melanoma and cutaneous T cell lymphoma[32-35]. M2 macrophages function through secreting functional mediator maresin 1, a member of the family of specialized pro-resolving mediators (SPMs) that are derived from enzymatic modification of polyunsaturated fatty acids (PUFAs)[36, 37]. Maresin 1, which is mainly secreted by M2 macrophages[36, 37], has been shown to have several important functions, such as promoting immune resolution[36, 37], promoting wound healing[38], shifting macrophage polarization toward M2, decreasing neuropathic pain[36, 39, 40], promoting tissue regeneration after resolution of inflammation[36, 41, 42], and promoting head regeneration of brown planaria nematode after surgical injury[36].

Although macrophages are increased in vitiligo skin[43,44], there have been no studies on macrophage polarization in either vitiligo or canities.

SUMMARY OF THE INVENTION

This invention is based in part on the discovery that specialized pro-resolving mediators (SPM) compounds described herein are melanocyte growth promoters and pro-survival factors. We also found that a deficiency of M2 macrophages or M2 functional mediator maresin 1 contributes to melanocyte depletion in vitiligo and canities. We further found that exogenous SPM compounds (for example, maresin 1) increased melanocyte survival in vitro. Fortuitously, it is also shown herein that maresin 1 significantly decrease melanocyte depletion in mouse models of vitiligo and canities and protecting melanocytes from depletion due to immune-independent causes. The invention provides compounds that may be suitable for the treatment of age-associated leukoderma and leukotrichia. The invention also provides compounds that may be suitable for the treatment of: dormant vitiligo lesions; chemically induced vitiligo; vitiligo that is non-responsive to inflammatory therapies; or canities.

In a first aspect, there is provided a method of promoting melanocyte growth and/or survival, the method including the administration, to a subject in need thereof, of one or more specialized pro-resolving mediators (SPMs) or a pharmaceutically acceptable salt, hydrate, or hydrated salt, or its optical isomer, racemate, diastereoisomer or enantiomer thereof, excluding lipoxin A4.

In a further aspect, there is provided a use of one or more specialized pro-resolving mediators (SPMs) or a pharmaceutically acceptable salt, hydrate, or hydrated salt, or its optical isomer, racemate, diastereoisomer or enantiomer thereof, excluding lipoxin A4, or a pharmaceutical composition thereof, for promoting melanocyte growth and/or survival.

In a further aspect, there is provided a use of one or more specialized pro-resolving mediators (SPMs) or a pharmaceutically acceptable salt, hydrate, or hydrated salt, or its optical isomer, racemate, diastereoisomer or enantiomer thereof, excluding lipoxin A4, or a pharmaceutical composition thereof in the manufacture of a medicament for promoting melanocyte growth and/or survival.

In a further aspect, there is provided a pharmaceutical composition for preventing or treating vitiligo including one or more SPM or a pharmaceutically acceptable salt, hydrate, or hydrated salt, or its optical isomer, racemate, diastereoisomer or enantiomer thereof, excluding lipoxin A4, as an active ingredient.

In a further aspect, there is provided a cosmetic composition for preventing or treating vitiligo or canities, the cosmetic composition including one or more SPM or a pharmaceutically acceptable salt, hydrate, or hydrated salt, or its optical isomer, racemate, diastereoisomer or enantiomer thereof, excluding lipoxin A4, as an active ingredient.

In a further aspect, there is provided a commercial package including (a) one or more SPMs or a pharmaceutically acceptable salt, hydrate, or hydrated salt, or its optical isomer, racemate, diastereoisomer or enantiomer thereof, excluding lipoxin A4; and (b) instructions for the use thereof for for promoting melanocyte growth and/or survival.

In a further aspect, there is provided a commercial package including (a) a pharmaceutical composition including one or more SPMs or a pharmaceutically acceptable salt, hydrate, or hydrated salt, or its optical isomer, racemate, diastereoisomer or enantiomer thereof, excluding lipoxin A4; and (b) instructions for the use thereof for promoting melanocyte growth and/or survival.

In a further aspect, there is provided a melanocyte growth media, the melanocyte growth media including one or more SPMs or a pharmaceutically acceptable salt, hydrate, or hydrated salt, or its optical isomer, racemate, diastereoisomer or enantiomer thereof, excluding lipoxin A4.

The SPM may be selected from one or more of the following: maresin 1; maresin 2; lipoxin B4; protectin D1; resolvin D2; and resolvin E1. The SPM or a pharmaceutically acceptable salt, hydrate, or hydrated salt, or its optical isomer, racemate, diastereoisomer or enantiomer thereof, may be maresin 1. The SPM or a pharmaceutically acceptable salt, hydrate, or hydrated salt, or its optical isomer, racemate, diastereoisomer or enantiomer thereof, may be maresin 2. The SPM or a pharmaceutically acceptable salt, hydrate, or hydrated salt, or its optical isomer, racemate, diastereoisomer or enantiomer thereof, may be lipoxin B4. The SPM or a pharmaceutically acceptable salt, hydrate, or hydrated salt, or its optical isomer, racemate, diastereoisomer or enantiomer thereof, may be protectin D1. The SPM or a pharmaceutically acceptable salt, hydrate, or hydrated salt, or its optical isomer, racemate, diastereoisomer or enantiomer thereof, may be resolvin D2. The SPM or a pharmaceutically acceptable salt, hydrate, or hydrated salt, or its optical isomer, racemate, diastereoisomer or enantiomer thereof, may be resolvin E1. The SPM may be selected from one or more of the following: maresin 1; maresin 2; lipoxin B4; epi-lipoxin B4; protectin D1; 22-hydroxy-protectin D1; protectin DX; 10-epi-protectin D1; resolvin D1; resolvin D2; resolvin D3; resolvin D4; resolvin D5; resolvin D6; resolvin E1; resolvin E2; and resolvin E3. Alternatively, the SPM or a pharmaceutically acceptable salt, hydrate, or hydrated salt, or its optical isomer, racemate, diastereoisomer or enantiomer thereof, may be may be selected from one or more of Formulas 1-12. The promoting of melanocyte growth and/or survival may prevent depigmentation of melanocytes and/or may promote re-pigmentation in non-inflammatory depigmentation of melanocytes. The melanocyte may be a skin melanocyte, a hair melanocyte, an eye melanocyte, or an ear melanocyte. The administration may be to reduce or reverse non-inflammatory loss of melanocytes. The administration may be for the treatment of age-associated leukoderma and leukotrichia. The promoting of melanocyte growth and/or survival, may be for the treatment of: dormant vitiligo lesions; chemically induced vitiligo; vitiligo that is non-responsive to inflammatory therapies; or canities. The vitiligo may be selected from: a dormant vitiligo lesion; a chemically induced vitiligo; and a vitiligo that is non-responsive to inflammatory therapies.

The administration may be as part of a combination therapy with phototherapy or an immune-suppressive therapy. The administration may be as part of a combination therapy with surgical melanocyte grafting therapy.

The pharmaceutical composition may be formulated for systemic delivery, via oral administration, intravenous injection, subcutaneous injection or intraperitoneal injection. The pharmaceutical composition may be formulated for topical administration. The cosmetic composition may be a formulation of: a lotion; a cream; an ointment; a suspension; a spray; or a coating on an adhesive tape.

DETAILED DESCRIPTION OF THE INVENTION

Figure 1A:
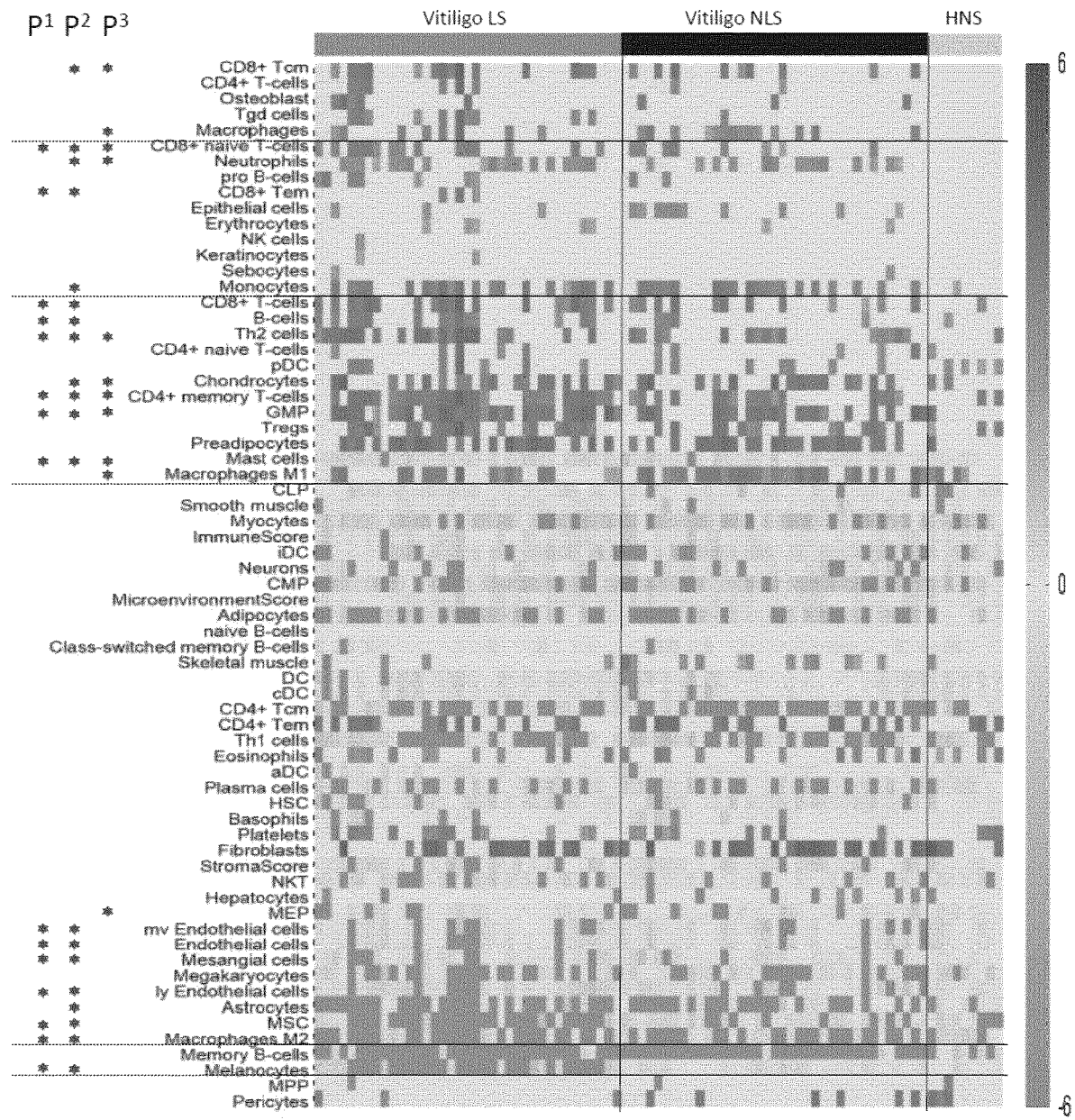
FIG. 1A shows immune cell profiles of Vitiligo Lesional and Non-Lesional Skin Relative to Healthy Normal Skin, wherein full thickness biopsies were obtained from the vitiligo lesional skin (LS, N=36), nonlesional skin (NLS, N=36) and healthy normal skin (HNS, N=9) and used for total RNA extraction; transcriptome sequencing was performed, followed by cellular deconvolution using the xCell algorithm, and the signatures of 64 recognizable cell types in each sample are presented as fold changes relative to the average of the HNS. * p<0.05 (p1: LS vs NLS; p2: LS vs HNS; p3: NLS vs HNS); Dashed horizontal lines highlight the melanocytes, M2 and other mono-macrophages as defined by xCell algorithm.

The following detailed description will be better understood when read in conjunction with the appended figures. For the purpose of illustrating the invention, the figures demonstrate embodiments of the present invention. However, the invention is not limited to the precise arrangements, examples, and instrumentalities shown.

Any terms not directly defined herein shall be understood to have the meanings commonly associated with them as understood within the art of the invention.

Compounds as described herein may be in the free form or in the form of a salt thereof. In some embodiment, compounds as described herein may be in the form of a pharmaceutically acceptable salt, which are known in the art (Berge S. M. et al., J. Pharm. Sci. (1977) 66(1):1-19). Pharmaceutically acceptable salt as used herein includes, for example, salts that have the desired pharmacological activity of the parent compound (salts which retain the biological effectiveness and/or properties of the parent compound and which are not biologically and/or otherwise undesirable). Compounds as described herein having one or more functional groups capable of forming a salt may be, for example, formed as a pharmaceutically acceptable salt. Compounds containing one or more basic functional groups may be capable of forming a pharmaceutically acceptable salt with, for example, a pharmaceutically acceptable organic or inorganic acid. Pharmaceutically acceptable salts may be derived from, for example, and without limitation, acetic acid, adipic acid, alginic acid, aspartic acid, ascorbic acid, benzoic acid, benzenesulfonic acid, butyric acid, cinnamic acid, citric acid, camphoric acid, camphorsulfonic acid, cyclopentanepropionic acid, diethylacetic acid, digluconic acid, dodecylsulfonic acid, ethanesulfonic acid, formic acid, fumaric acid, glucoheptanoic acid, gluconic acid, glycerophosphoric acid, glycolic acid, hemisulfonic acid, heptanoic acid, hexanoic acid, hydrochloric acid, hydrobromic acid, hydriodic acid, 2-hydroxyethanesulfonic acid, isonicotinic acid, lactic acid, malic acid, maleic acid, malonic acid, mandelic acid, methanesulfonic acid, 2-napthalenesulfonic acid, naphthalenedisulphonic acid, p-toluenesulfonic acid, nicotinic acid, nitric acid, oxalic acid, pamoic acid, pectinic acid, 3-phenylpropionic acid, phosphoric acid, picric acid, pimelic acid, pivalic acid, propionic acid, pyruvic acid, salicylic acid, succinic acid, sulfuric acid, sulfamic acid, tartaric acid, thiocyanic acid or undecanoic acid. Compounds containing one or more acidic functional groups may be capable of forming pharmaceutically acceptable salts with a pharmaceutically acceptable base, for example, and without limitation, inorganic bases based on alkaline metals or alkaline earth metals or organic bases such as primary amine compounds, secondary amine compounds, tertiary amine compounds, quaternary amine compounds, substituted amines, naturally occurring substituted amines, cyclic amines or basic ion-exchange resins. Pharmaceutically acceptable salts may be derived from, for example, and without limitation, a hydroxide, carbonate, or bicarbonate of a pharmaceutically acceptable metal cation such as ammonium, sodium, potassium, lithium, calcium, magnesium, iron, zinc, copper, manganese or aluminum, ammonia, benzathine, meglumine, methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, glucamine, methylglucamine, theobromine, purines, piperazine, piperidine, procaine, N-ethylpiperidine, theobromine, tetramethylammonium compounds, tetraethylammonium compounds, pyridine, N,N-dimethylaniline, N-methylpiperidine, morpholine, N-methylmorpholine, N-ethylmorpholine, dicyclohexylamine, dibenzylamine, N,N-dibenzylphenethylamine, 1-ephenamine, N,N'-dibenzylethylenediamine or polyamine resins. In some embodiments, compounds as described herein may contain both acidic and basic groups and may be in the form of inner salts or zwitterions, for example, and without limitation, betaines. Salts as described herein may be prepared by conventional processes known to a person skilled in the art, for example, and without limitation, by reacting the free form with an organic acid or inorganic acid or base, or by anion exchange or cation exchange from other salts. Those skilled in the art will appreciate that preparation of salts may occur in situ during isolation and purification of the compounds or preparation of salts may occur by separately reacting an isolated and purified compound.

In some embodiments, compounds and all different forms thereof (e.g. free forms, salts, polymorphs, isomeric forms) as described herein may be in the solvent addition form, for example, solvates. Solvates contain either stoichiometric or non-stoichiometric amounts of a solvent in physical association the compound or salt thereof. The solvent may be, for example, and without limitation, a pharmaceutically acceptable solvent. For example, hydrates are formed when the solvent is water or alcoholates are formed when the solvent is an alcohol.

In some embodiments, compounds and all different forms thereof (e.g. free forms, salts, solvates, isomeric forms) as described herein may include crystalline and amorphous forms, for example, polymorphs, pseudopolymorphs, conformational polymorphs, amorphous forms, or a combination thereof. Polymorphs include different crystal packing arrangements of the same elemental composition of a compound. Polymorphs usually have different X-ray diffraction patterns, infrared spectra, melting points, density, hardness, crystal shape, optical and electrical properties, stability and/or solubility. Those skilled in the art will appreciate that various factors including recrystallization solvent, rate of crystallization and storage temperature may cause a single crystal form to dominate.

In some embodiments, compounds and all different forms thereof (e.g. free forms, salts, solvates, polymorphs) as described herein include isomers such as geometrical isomers, optical isomers based on asymmetric carbon, stereoisomers, tautomers, individual enantiomers, individual diastereomers, racemates, diastereomeric mixtures and combinations thereof, and are not limited by the description of the formulas illustrated for the sake of convenience.

In some embodiments, pharmaceutical compositions as described herein may comprise a salt of such a compound, preferably a pharmaceutically or physiologically acceptable salt. Pharmaceutical preparations will typically comprise one or more carriers, excipients or diluents acceptable for the mode of administration of the preparation, be it by injection, inhalation, topical administration, lavage, or other modes suitable for the selected treatment. Suitable carriers, excipients or diluents (used interchangeably herein) are those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non water soluble compounds such as those used for vitamin K. For enteral administration, the compound may be administered in a tablet, capsule or dissolved in liquid form. The tablet or capsule may be enteric coated, or in a formulation for sustained release. Many suitable formulations are known, including, polymeric or protein microparticles encapsulating a compound to be released, ointments, pastes, gels, hydrogels, or solutions which can be used topically or locally to administer a compound. A sustained release patch or implant may be employed to provide release over a prolonged period of time. Many techniques known to one of skill in the art are described in Remington: the Science & Practice of Pharmacy by Alfonso Gennaro, 20th ed., Lippencott Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene polyoxypropylene copolymers may be used to control the release of the compounds. Other potentially useful parenteral delivery systems for modulatory compounds include ethylene vinyl acetate copolymer particles, osmotic pumps, implantable infusion systems, and liposomes. Formulations for inhalation may contain excipients, for example, lactose, or may be aqueous solutions containing, for example, polyoxyethylene 9 lauryl ether, glycocholate and deoxycholate, or may be oily solutions for administration in the form of nasal drops, or as a gel.

Compounds or pharmaceutical compositions as described herein or for use as described herein may be administered by means of a medical device or appliance such as an implant, graft, prosthesis, stent, etc. Also, implants may be devised which are intended to contain and release such compounds or compositions. An example would be an implant made of a polymeric material adapted to release the compound over a period of time.

An "effective amount" of a pharmaceutical composition as described herein includes a therapeutically effective amount or a prophylactically effective amount. A "therapeutically effective amount" refers to an amount effective, at dosages and for periods of time necessary, to achieve the desired therapeutic result, such as reduced vitiligo or canities, increased melanocyte growth and/or survival or prevention of depigmentation of melanocytes and/or promotion of re-pigmentation in non-inflammatory depigmented melanocytes. A therapeutically effective amount of a compound may vary according to factors such as the disease state, age, sex, and weight of the subject, and the ability of the compound to elicit a desired response in the subject. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result. Typically, a prophylactic dose is used in subjects prior to or at an earlier stage of disease, so that a prophylactically effective amount may be less than a therapeutically effective amount.

It is to be noted that dosage values may vary with the severity of the condition to be alleviated. For any particular subject, specific dosage regimens may be adjusted over time according to the individual need and the professional judgment of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

Maresin 1 is a member of a growing family of fatty acid-derived specialized pro-resolving mediators (SPMs), which also include protectins, resolvins (D series and E series), and lipoxins. Maresins, protectins and D series of resolvins are derivatives of an omega-3 fatty acid docosahexaenoic acid (DHA, 22:6(n−3)), while E series of resolvins are derived from another omega-3 fatty acid eicosapentaenoic acid (EPA, 20:5(n−3)). In contrast, lipoxins are derived from an omega-6 fatty acid, linoleic acids (LA, 18:2 (n−6)). LA also gives rise to pro-inflammatory mediators (leukotrienes and prostaglandins). It is of note that in addition to maresin1, protectins and resolvins also have strong pro-survival effects on cultured human epidermal melanocytes, a function not shared by lipoxin A4, which not only did not protect melanocytes from physiological distress, it accelerated melanocyte depletion. Therefore, all the SPMs are not interchangeable in their ability to protect melanocytes or melanocyte precursors, which may have implications in the development of therapies based on SPMs for the treatment of depigmentation diseases or other medical conditions in the future. However, as demonstrated herein maresin 1; maresin 2; lipoxin B4; protectin D1; resolvin D2; and resolvin E1 all show ability to protect melanocytes.

Maresin 1 (macrophage mediator in resolution of inflammation 1) is a small molecule (molecular weight=363) derivative of docosahexaenoic acid (DHA, an omega-3 fatty acid) through 15 lipoxygenase-mediated oxygenation. To date, two types of cellular receptors have been found, G-protein coupled receptor LGR6 and nuclear receptor RORα. RORα is expressed by multiple skin cell types, including the melanocytes, whereas LGR6 is not expressed by melanocytes.

Such salts may be used in the pharmaceutical field, for example, conventional acid addition salts used in external preparations for skin such as salts derived from inorganic acids such as hydrochloric acid, bromic acid, sulfuric acid, sulfamic acid, phosphoric acid or nitric acid and salts derived from organic acids such as acetic acid, and organic acids such as glycolic acid, stearic acid, citric acid, maleic acid, malonic acid, methanesulfonic acid, tartaric acid, malic acid, phenylacetic acid, glutamic acid, benzoic acid, salicylic acid, 2-acetoxybenzoic acid, fumaric acid, toluenesulfonic acid, oxalic acid or trifluoroacetic acid. The salt may be a base addition salt such as ammonium, dimethylamine, monomethylamine, monoethylamine or diethylamine. In addition, the salt may be in the form of a conventional metal salt, for example, a salt derived from a metal such as sodium, potassium, lithium, magnesium, or calcium. The acid addition salt, the base addition salt or the metal salt may be produced by a conventional method.

Maresin 1 (MaR1) is a lipoxygenase (LOX) metabolite derived from omega-3 fatty acid, docosahexaenoic acid (DHA), and is a specialized pro-resolving mediator (SPM). Maresin 1 may be 7R, 14S-dihydroxy-4Z, 8E, 10E, 12Z, 16Z, 19Z-docosahexaenoic acid (CAS #1268720-28-0) may have the structure of Formula 1 below.

Formula 1

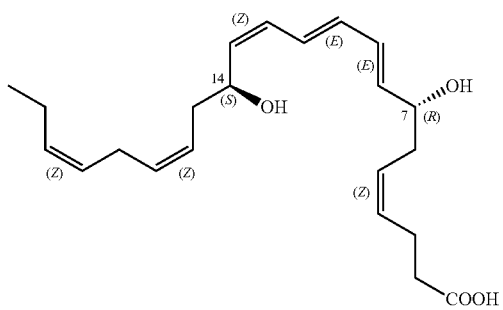

Maresin 1 may also be in the form of a pharmaceutically acceptable salt thereof. For example, a base addition salt or a metal salt can be prepared by reacting the ionic form of maresin 1 may have an appropriate base or metal ion or the like. A pharmaceutically acceptable salt of maresin 1 may have the structure of Formula 2 below.

Formula 2

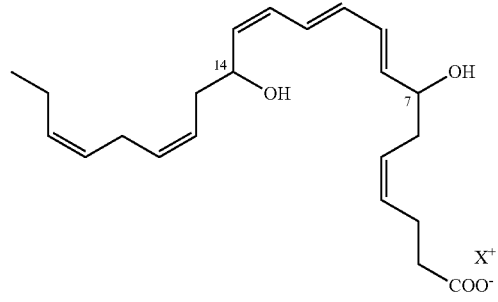

In Formula 2, $X^+$ may for example, represent sodium, potassium, lithium, magnesium, or calcium. The pharmaceutically acceptable salt of maresin 1 may be sodium 7R, 14S-dihydroxy-4Z, 8E, 10E, 12Z, 16Z, 19Z-docosahexaenoic acid or may be potassium 7R, 14S-dihydroxy-, 10E, 12Z, 16Z, 19Z-docohexaenoic acid. Maresin 1 may also be in the form of a solvate thereof.

Maresin 2 (CAS #1639809-46-3), 13R,14S-dihydroxy-4Z,7Z,9E,11E,16Z,19Z-docosahexaenoic acid, as represented by Formula 3 below is another tested SPM.

Formula 3

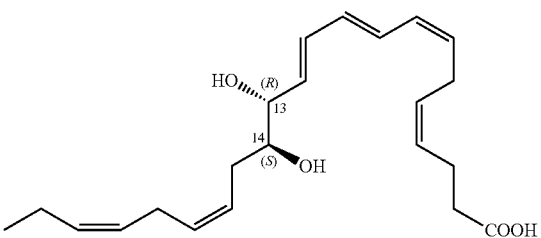

Alternatively, a pharmaceutically acceptable salt of maresin 2 may have the structure of Formula 4 below.

Formula 4

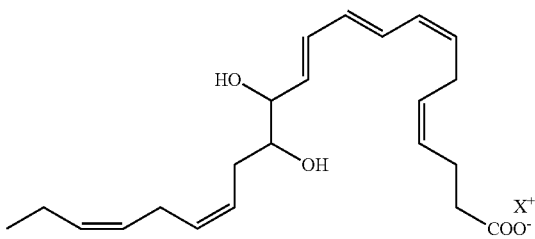

Lipoxin B4 (CAS #98049-69-5), 5S,14R,15S-trihydroxy-6E,8Z,10E,12E-eicosatetraenoic acid, as represented by Formula 5 below is another tested SPM.

Formula 5

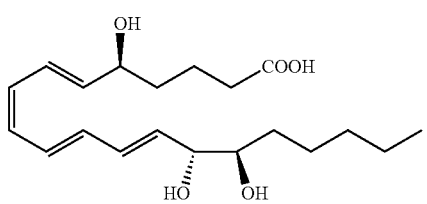

Alternatively, a pharmaceutically acceptable salt of lipoxin B4 may have the structure of Formula 6 below.

Formula 6

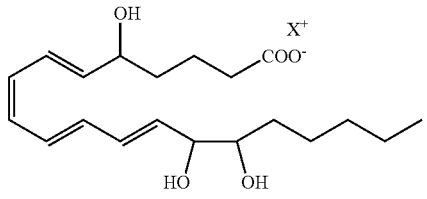

Protectin D1 (CAS #660430-03-5), 10R,17S-dihydroxy-4Z,7Z,11E,13E,15Z,19Z-docosahexaenoic acid, as represented by Formula 7 below is another tested SPM.

Formula 7

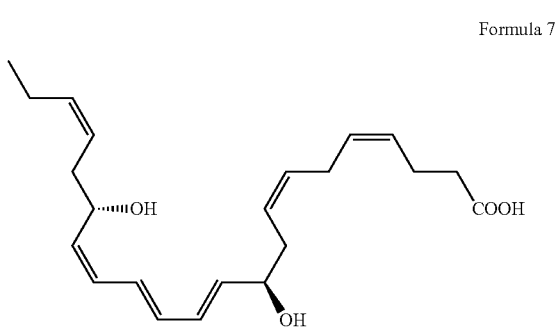 [SMILES: CC/C=C\C[C@H](O)\C=C/C=C/C=C/[C@H](O)C/C=C\C/C=C\CCC(=O)O]

Alternatively, a pharmaceutically acceptable salt of protectin D1 may have the structure of Formula 8 below.

Formula 8

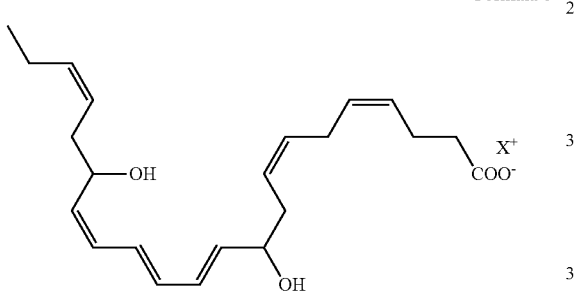

Resolvin D2 (CAS #810668-37-2), 7S,16R,17S-trihydroxy-4Z,8E,10Z,12E,14E,19Z-docosahexaenoic acid (4Z,7S,8E,10Z,12E,14E,16R,17S,19Z)-7,16,17-trihydroxydocosa-4,8,10,12,14,19-hexaenoic Acid, as represented by Formula 9 below is another tested SPM.

Formula 9

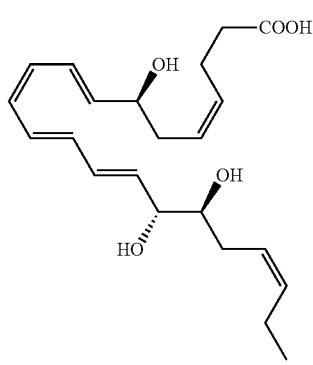

Alternatively, a pharmaceutically acceptable salt of resolvin D2 may have the structure of Formula 10 below.

Formula 10

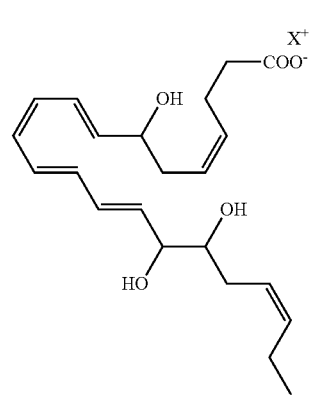

Resolvin E1 (CAS #552830-51-0), 5S,12R,18R-trihydroxy-6Z,8E,10E,14Z,16E-eicosapentaenoic acid, as represented by Formula 11 below is another tested SPM.

Formula 11

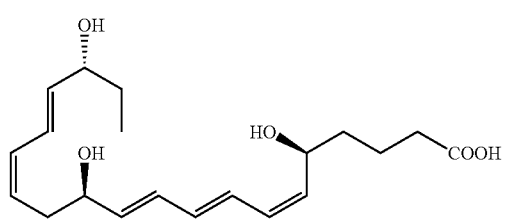

Alternatively, a pharmaceutically acceptable salt of resolvin E1 may have the structure of Formula 12 below.

Formula 12

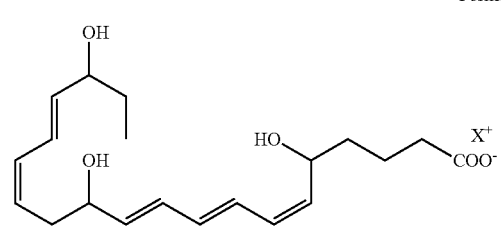

"Solvate" as used herein means a complex or aggregate formed by one or more solute molecules, i.e., a suitable SPM or a pharmaceutically acceptable salt thereof, and one or more solvent molecules. The solvate may be, for example, a complex or aggregate formed with water, methanol, ethanol, isopropanol or acetic acid.

A suitable SPM as described herein may also be in the form of its stereoisomer. The stereoisomers include all stereoisomers such as enantiomers and diastereomers. The compound may be a stereoisomerically pure form or a mixture of one or more stereoisomers, for example, a racemic mixture. The separation of certain stereoisomers can be carried out by any of the conventional methods known in the art.

"Active ingredient" is intended to carry out the function referred to in the composition and excludes those that do not fulfill the function as they are included in minor amounts as impurities.

A suitable SPM as described herein may be chemically synthesized or commercially available or extracted from natural sources.

The compositions of suitable SPMs as described herein may be one that promotes melanocyte growth and/or survival.

The composition may comprise a "therapeutically effective amount" of a suitable SPM or a pharmaceutically acceptable salt, solvate, or combination thereof. In this composition, "therapeutically effective amount" means an amount sufficient to exhibit a therapeutic effect when administered to a subject or a cell in need thereof. "Treatment" means treating a disease or medical condition in a mammal, including a human, including an individual, which includes: (a) preventing the occurrence of the disease or medical condition, cure; (b) relieving the disease or medical condition, i.e., eliminating or ameliorating the disease or medical condition in the patient; (c) inhibiting the disease or medical condition, i.e. slowing or stopping the progression of the disease or medical condition in the individual; or (d) relieving the disease or medical condition in the subject. In particular, one that promotes melanocyte growth and/or survival.

The one or more specialized pro-resolving mediators (SPMs) or a pharmaceutically acceptable salt, hydrate, or hydrated salt, or its optical isomer, racemate, diastereoisomer or enantiomer thereof, excluding lipoxin A4, may be present in an amount of from 0.001% to 80%, such as from 0.01% to 60%, from 0.01% to 40%, from 0.01% to 30%, from 0.01% to 20% %, 0.01% to 10%, 0.01% to 5%, 0.05% to 60%, 0.05% to 40%, 0.05% to 30%, 0.05% to 20% From 0.05% to 10%, from 0.05% to 5%, from 0.1% to 60%, from 0.1% to 40%, from 0.1% to 30%, from 0.1% to 20% % to 10% by weight, or 0.1% to 5% by weight of SPM as described herein. In particular, for topical vitiligo treatments a 0.01% maresin 1 was tested.

Drug delivery compositions may be prepared and utilized to treat or prevent a variety of diseases or conditions, particularly where the treatment site contains melanocytes. For example, skin melanocytes, hair melanocytes, eye melanocytes, or ear melanocytes to deliver SPMs described herein to promote melanocyte growth and/or survival. The SPM may be selected from one or more of the following: maresin 1; maresin 2; lipoxin B4; protectin D1; resolvin D2; and resolvin E1. The composition described herein may be used for the prevention of depigmentation of melanocytes and/or promoting re-pigmentation in non-inflammatory depigmentation of melanocytes. Examples of diseases or conditions that may be treated, may for example, include age-associated leukoderma and leukotrichia; dormant vitiligo lesions; chemically induced vitiligo; vitiligo that is non-responsive to inflammatory therapies; and canities.

Materials and Methods

Study Subjects and Skin Biopsies:

This study was approved by the Clinical Ethics Board of University of British Columbia. For transcriptome sequencing and cellular profiling experiments, 4 mm punch biopsies were obtained from the lesional and nonlesional skin of 36 vitiligo patients (29 with generalized vitiligo and 7 with segmental vitiligo), 15 patients with chronic eczema, and healthy skin from 9 volunteers as described previously[45]. The biopsies were bisected, with % placed immediately in RNA Later solution (Life Labs™) and stored at −20° until further use. The other ½ placed in formalin for histological assessment. For flow cytometry analysis of macrophages in vitiligo patients, 5 mm punch biopsies were obtained from the lesional, border and non-lesional skin, and immediately placed in saline for cell isolation (See below).

RNA Extraction and Transcriptome Sequencing:

Bulk RNA was extracted from skin biopsies using the RNeasy™ Fibrous Tissue Mini Kit as we had described previously[14, 46], and used for transcription sequencing by Novo Gene™ (Tianjin China) using the Illumina™ platform (HiSeq PE150), generating at least 30 million clean reads for each sample. The expression of each transcript was normalized to the total number of transcripts and the length of the transcripts and expressed in FPKM. Ingenuity Pathway Analysis™ (IPA) was used for analysis of differentially expressed genes between lesional and nonlesional skin, and between skin biopsies from vitiligo and chronic eczema patients and the skin biopsies from health controls using two fold change and $p<0.05$ as the cut off for statistical significance using R program.

In Silico Profiling of Cellular Infiltrates in Skin Biopsies:

We used xCell tool developed by Aron et al.[47, 48] to evaluate the relative changes in recognizable immune cells in the skin biopsies. Increasingly used for in silico analysis of cellular infiltrates in inflammatory as well as malignant diseases[49-52], this method is based on the validated gene expression signatures of 64 types of cells involved in inflammation and immune responses, and is capable of estimating the relative abundance of the immune-active cells present in the tissue biopsies. In addition, a composite score (ImmuneScore™) is generated for estimation of the general extent of immune response in a given tissue.

Isolation and Detection of M1 and M2 Macrophages in Skin Biopsies by Flow Cytometry For isolation of macrophages from human vitiligo skin: 5 mm punch biopsies were minced finely with scissors and mixed with 3 ml digestion buffer containing 0.8 mg/ml Collagenase IV and 0.03 mg/ml DNAse (Sigma Aldrich™), 10% FBS, 1% penicillin/streptomycin in RPMI medium. Samples were incubated overnight in 5% $CO_2$ at 37° C., then harvested in PBS, filtered through a 100-μm strainer and centrifuged. Surface staining antibody panel included anti-humans CD11b-Alexa Fluor488™, CD163-BV421™ and CD80-Alexa fluor 647™ (Biolegen™). Cells were incubated with antibodies for 30 min at 4° C., washed in PBS containing 1% FCS and analyzed using LSRII™ cell sorter (BD Biosciences™).

For isolation of macrophages from murine skin: 1 cm×1 cm sized skin samples were cut into small pieces, placed in a solution of PBS containing 1 mg/ml dispase (Roche™) and incubated for 1 hour at 37° C. The samples were then transferred into RPMI containing 1 mg/ml Collagenase IV and 0.1 mg/ml DNAse (Sigma Aldrich™) and incubated for 90 minutes at 37° C. Single cell suspension was prepared by passing through 100 μm strainer. Cells were washed and stained in PBS without $Ca^{2+}$ and $Mg^{2+}$ supplemented with 1% heat-inactivated FCS. Cell surface staining panel included anti-mouse CD163-BV421™, CD80-Alexa fluor 647™, and CD11b-Percp Cy5.5™ (Biolegend™) for 30 minutes at 4° C. Cells were washed with PBS and analyzed with LSRII™ cell sorter (BD Biosciences™).

B6 Mouse Model of Vitiligo with TRP2 Immunization

Eight week old female C57BL/J6 mice were ordered from The Jackson Laboratory™, and fed a standard diet of Animal Care Facility of Vancouver Coastal Health Research institute (4 mice/cage). For induction of vitiligo, mice were immunized by intradermal injections (ID, starting at Day 0) at the left hock, and repeated at 2-week, using the method described by S. You et al. that efficiently induces melanocyte specific CD8+ T cell responses[53]. The immunogen consisted of TRP2-180 (50 µg) peptide mixed with LPS (5 µg) and CpG ODN 1826 (5 µg) in 50 µL of PBS solution per mouse per injection. Immunization response score was recorded at 48 hours after the first immunization by evaluating the redness and swelling (0=none, 1=mild, 2=moderate, 3=severe). For assessing macrophage M1 and M2 populations, the TRP-immunized and non-immunized mice were anaesthetized 48 hours after immunization for skin sampling at the immunization site and used for cell isolation as described above.

Figure 5:
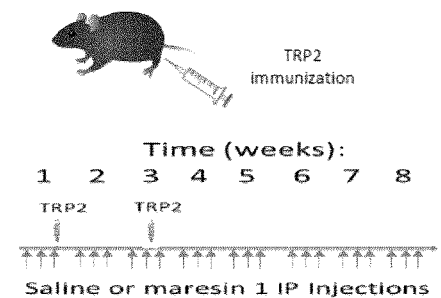
FIG. 5 shows the effects of maresin 1 on melanocyte depletion in B6 mouse Vitiligo model; (A) shows C57BL/J6 mice at 8 weeks of age were treated with IP injections of saline (N=20) or maresin 1 (800 ng/mouse, N=20) three times a week for 8 weeks and each mouse received TRP2 immunization by intradermal injections (ID) to the left hock at the end of week 1, and repeated at the end of week 3, wherein the mice were observed and photographed weekly for assessing depigmentation at the immunization site; (B) shows representative photographs of mice receiving saline IP or Maresin IP; (C) shows A depigmentation scoring template was used to measure the extent of depigmentation at each weekly assessment and the average depigmentation scores of the Saline IP or Maresin IP treated groups were plotted in (D); the peak immunization reaction scores (0-6) of the saline or maresin 1 treated groups; (E) shows a peak immunization reaction score, measured by combining erythema (0-3) and edema (0-3) at 48 hours after immunization; (F) shows he reduction of vitiligo depigmentation achieved by maresin 1 treatment was strongly correlated with the degree of reduction of immunization score. (p<00001, Deming Regression). * p<0.05 (two tailed t test).
Figure 5:
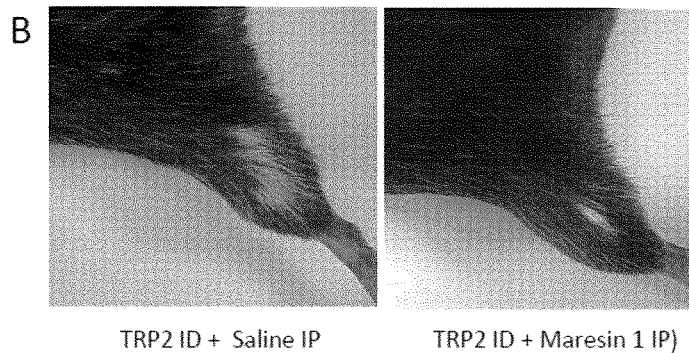
Figure 5:
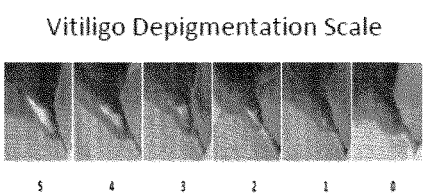
Figure 5:
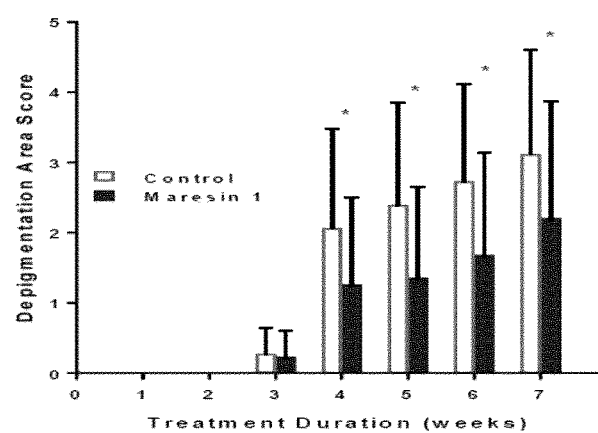
Figure 5:
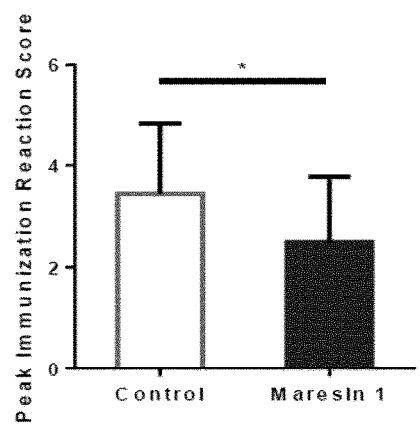
Figure 5:
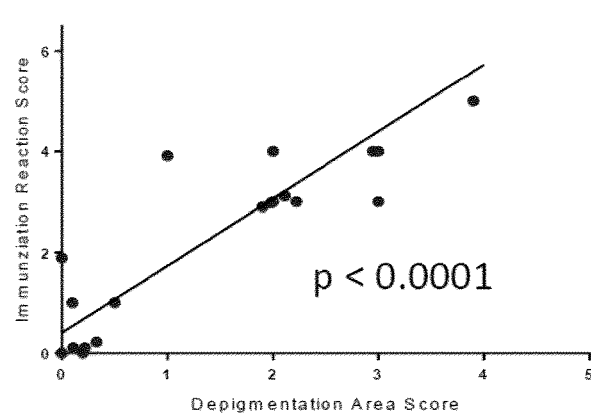

For assessing the effects of maresin 1 treatment, C57BL/J6 mice were randomly assigned to the sham injection control group (200 µl saline IP, n=20) and the Maresin 1 injection group (800 ng in 200 µl saline IP, n=20). All mice received three IP pre-treatments before the first immunization and continued to receive IP injections 3 times per week till the end of study. Mice were monitored 5 times per week and evaluated using a Depigmentation Area Scoring Template (0-5) (FIG. 5C).

At the end of the study (Day 35), after photography, the mice were euthanized and full-thickness skin biopsies (1 cm by 1 cm) of the left hock immunization sites were collected with surgical scissors. Half of the sample was store in RNAlater™ for RNA extraction and the other half was fixed in OCT embedding medium for histopathology analysis. Spleen and inguinal lymph node tissues were collected for immunohistochemistry and RNA isolation.

B6 Mouse Model of Canities and Serum Maresin Quantification

To observe aging-associated spontaneous hair greying (canities), C57BL/J6 mice aged 8 weeks were purchased from JAX Labs™ and kept in standard conditions for 8 weeks. The fur color as well as overall appearance and behaviors were monitored daily by visual inspection and by photography. By 6-8 weeks, about 20-40% of the mice would develop spontaneous canities. At the end of observation, central venous blood was collected and used for ELISA analysis using maresin 1 ELISA kit (Caymen Chemicals™) following the manufacturers' recommended protocol with purified maresin 1 serving as the chemical standard.

Effects of Maresin 1 on Canities Development in B6 Mice

C57BL/J6 mice from The Jackson Laboratory™, 8 weeks of age were divided into two groups that received intraperitoneal injections of maresin 1 (800 ng in 100 µl saline) or saline alone three times a week for 6 weeks. The mice were observed at weekly intervals by visual inspection. At the end of the experiment, the mice were photographed and weighed.

Melanocyte Proliferation and Survival Assay In Vitro

Human neonatal epidermal melanocytes (HEMn-DP) were purchased from ThermoFisher Scientific™ (C-202-5C). Melanocytes were cultured in full growth medium (Medium 254 supplemented with Human Melanocyte Growth Supplement, both purchased from ThermoFisher Scientific™. Cells were expanded and passaged 3 times before conducting the assay. $4\times10^3$ melanocytes per well were seeded into 96 well plate and allowed to recover for 4 hours before the treatment was added for each condition in 100 µl final volume. Cells were treated and kept in 37° C., 5% $CO_2$ for 3 days. Viability assay was conducted using CellTiter-Blue Cell Viability Assay Kit™ (Promega™, G8080) and signal was measured using GlowMax™ plate reader (Promega™) after 4 hours at 37° C., 5% $CO_2$. Merasin 1 (Cayman™) was diluted into 1 µg/ml using PBS and added to the culture medium at concentrations ranging from 0 to 1 µg/ml. For survival assays, the procedure was essentially the same as proliferation assay except that melanocytes were kept in M254 medium without human melanocyte growth supplement. The assays were conducted in triplicates.

EXAMPLES

Figure 1B:
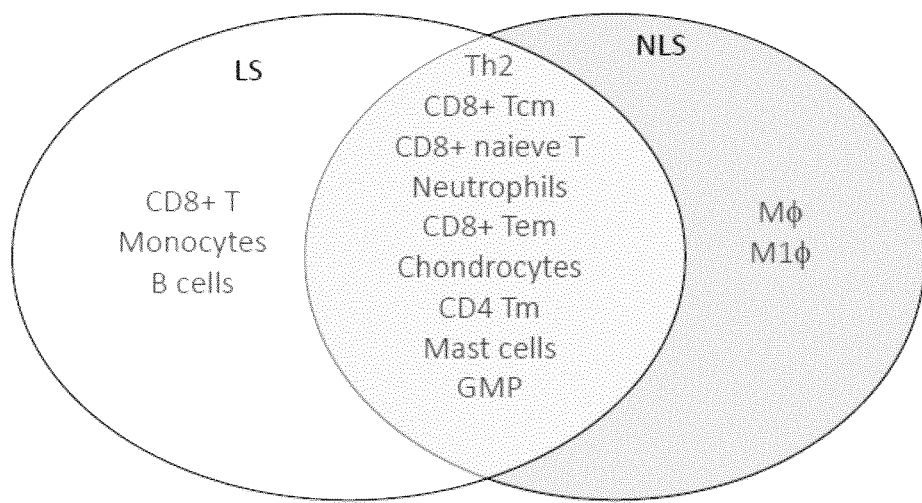
FIG. 1B shows that most cells with enrichment in vitiligo LS are also enriched in vitiligo NLS.
Figure 1C:
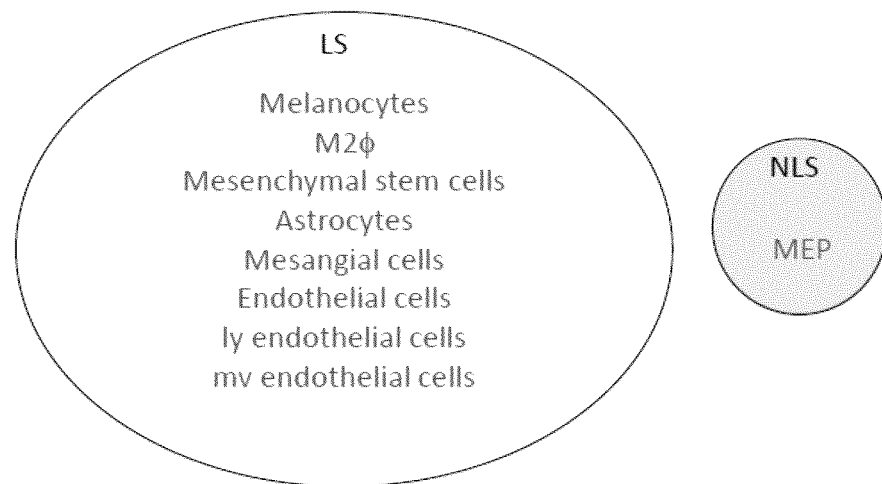
FIG. 1C shows that cells depleted in vitiligo LS are not depleted in vitiligo NLS.

Example 1: In Silico Profiling of Immune Cell Landscape Reveals M2 Macrophage Deficiency in Vitiligo Lesional Skin Microenvironment, but not in Vitiligo Nonlesional Skin or Skin Affected by Eczema To gain sights into the cellular changes preferentially present in the microenvironment of vitiligo lesional skin, we performed whole transcriptome sequencing followed by cellular deconvolution analysis on vitiligo lesional skin, using vitiligo non-lesional skin, and skin biopsies from healthy volunteers and eczema patients as the controls. Of the 64 cell types evaluable by xCell method, 14 types of cells showed significant enrichment in vitiligo skin biopsies compared with healthy normal skin (FIG. 1A), including cells involved in innate immunity (monocytes, macrophages and M1 macrophages) and adaptive immunity (such as CD8+, CD4+ T cells). Of these, the majority (including CD8+T cm, CD8+ naïve T, neutrophils, CD8+ Tem, Th2, chondrocytes, CD4+ memory T, GMP, and mast cells) were enriched in both lesional and nonlesional vitiligo skin (FIG. 1B). In contrast, 7 types of cells showed significant depletion specifically in vitiligo lesional skin compared with healthy normal skin, but not in vitiligo nonlesional skin, including melanocytes, M2 macrophages, mesenchymal stem cells (MSC), mesangial cells, endothelial cells, ly endothelial cells, and my endothelial cells (FIG. 1C).

Figure 2:
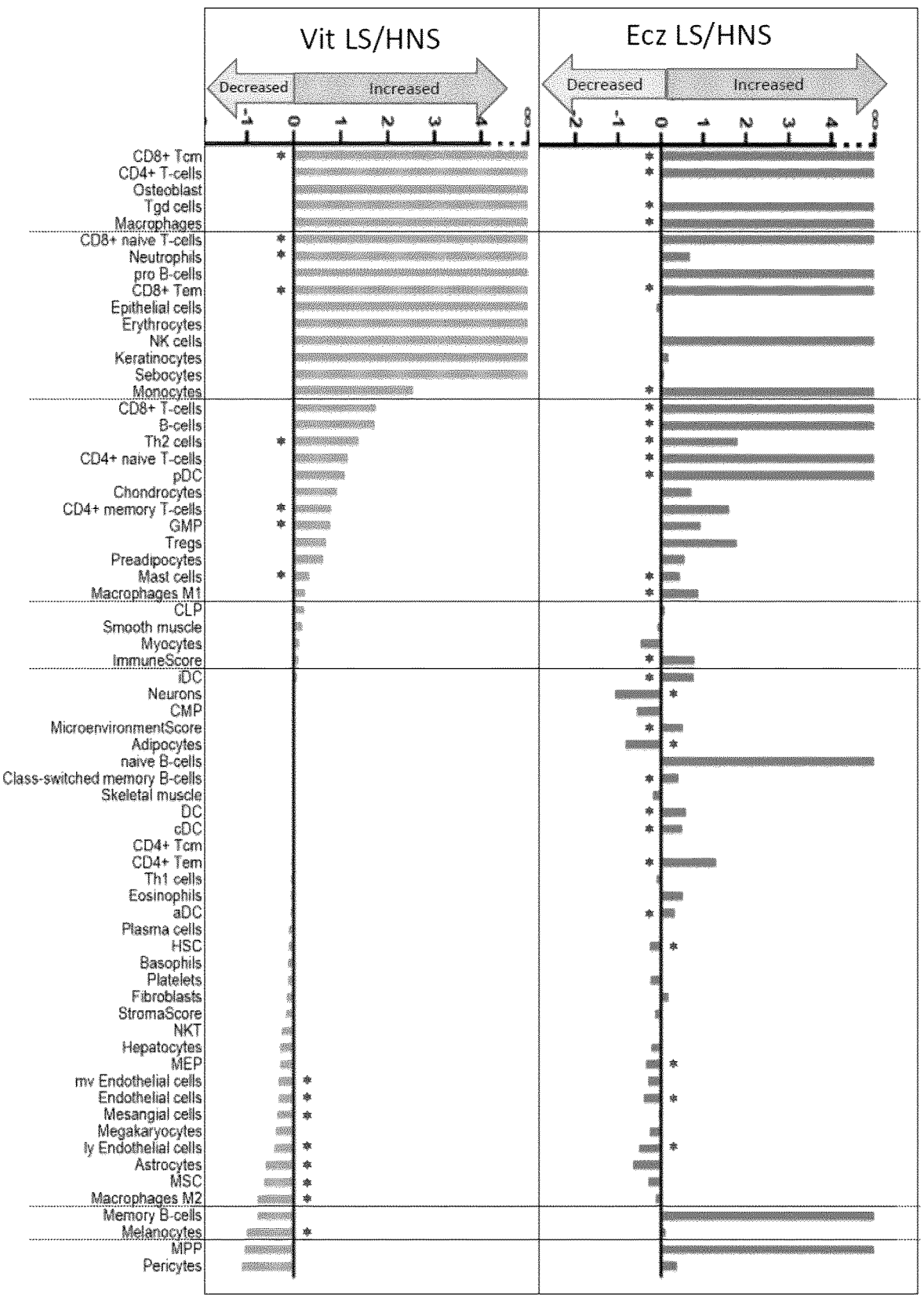
FIG. 2 shows a waterfall plot of distinct cell profiles of Vitiligo LS and Eczema LS, wherein the cells were ranked in descending order of their fold changes (FC) in vitiligo LS (Left Panel) relative to healthy normal skin (HNS), with the FC values; and the Right Panel shows the enrichment or depletion of these cells in eczema LS relative to HNS (asterisks indicate the changes reaching statistical significance, with p<0.05).

To understand if the cellular changes observed in vitiligo lesional skin is specific for this immune mediated skin condition, we performed the same analysis on skin biopsies from patients with chronic eczema, a prototypical Th2 immune mediated inflammatory skin disease. As shown in FIG. 2 the cells that were enriched in vitiligo lesional skin were in general also enriched in eczema lesional biopsies. However, the cells with depletion in vitiligo lesional skin were not depleted in eczema lesional skin, suggesting that the depletion of melanocytes and other cells (such as M2 macrophages) was specific for vitiligo skin lesions.

Figure 9:
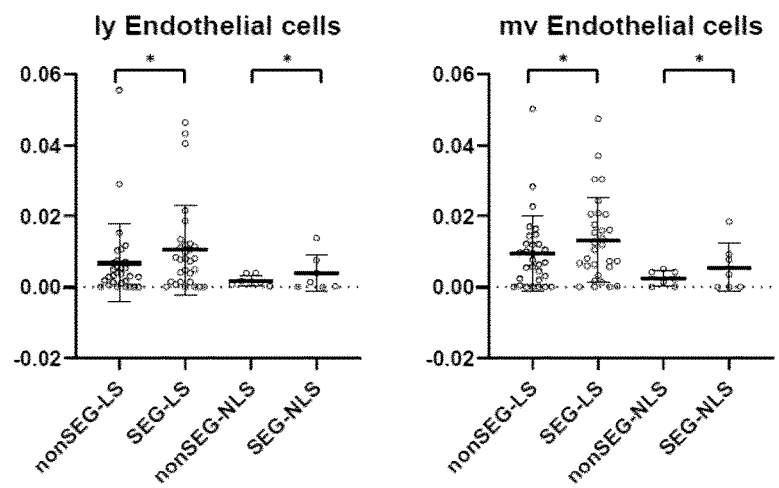
FIG. 9 shows Vitiligo lesional skin cells with significant differences between segmental vitiligo and generalized (nonsegmental) vitiligo.
Figure 10:
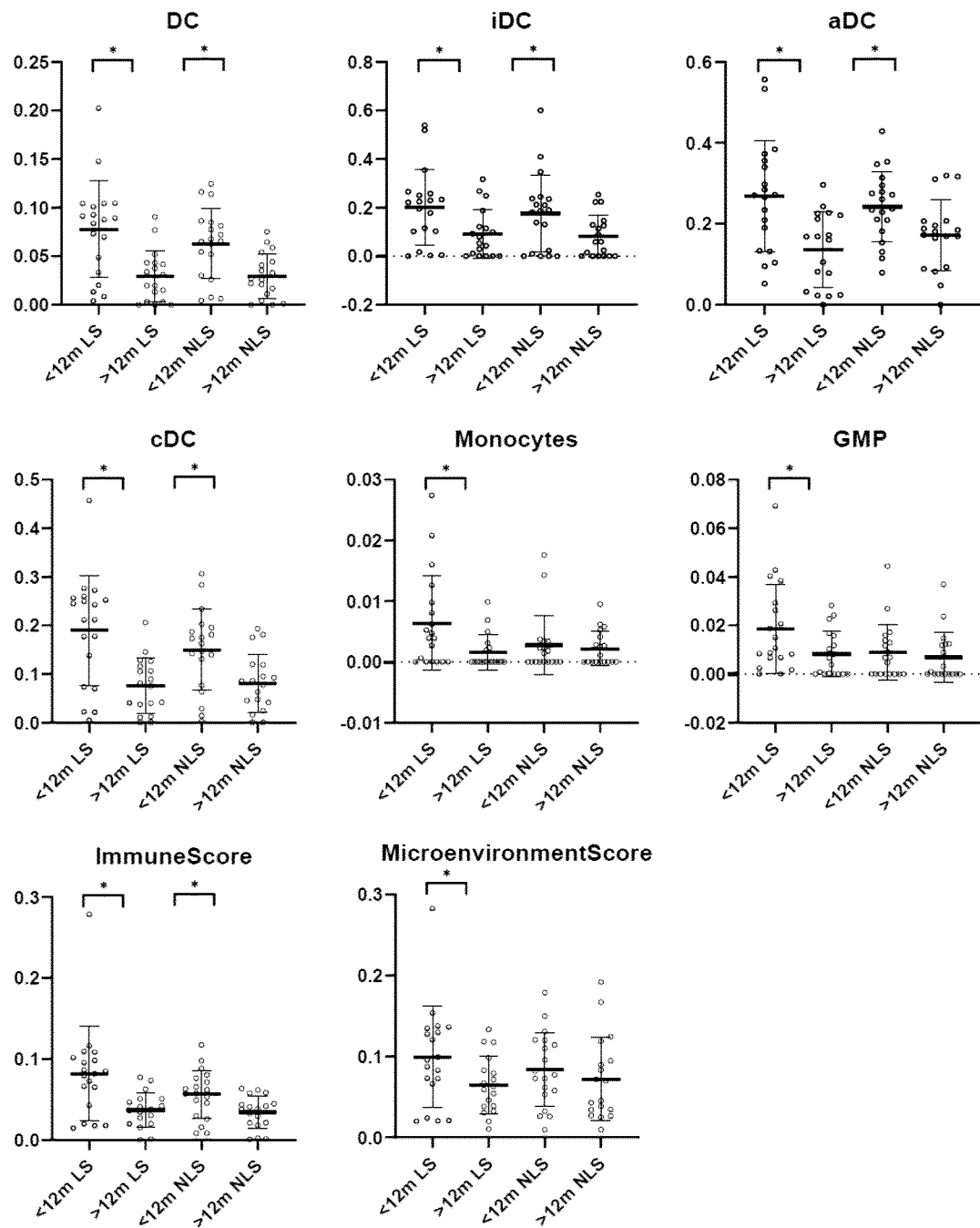
FIG. 10 shows Vitiligo lesional skin cells with significant differences between recent onset lesions or distant onset lesions of vitiligo.

To test if the lesional cellular infiltrates are correlated with vitiligo subtypes or disease stages, we stratified the vitiligo patients into morphological groups (generalized vs segmental vitiligo) or disease duration groups (active vitiligo with onset within 12 months, vs relatively stable vitiligo with duration longer than 12 months). Of the 36 vitiligo individuals analyzed, 29 had generalized vitiligo, and 7 had segmental vitiligo. Two types of cells showed significant differences between segmental vitiligo and generalized vitiligo, ly endothelial cells and my endothelial cells (FIG. 9). These cells were depleted in generalized vitiligo but not in segmental vitiligo. When compared with vitiligo that had been present for more than 12 months, vitiligo lesions with shorted disease duration (typically more active or progressive) had much higher immune score, and more significant enrichment of monocytes, granulocyte-monocyte progenitor cells and dendritic cells (FIG. 10), suggesting that there is higher immunological reactions in early stages of vitiligo development.

Figure 3:
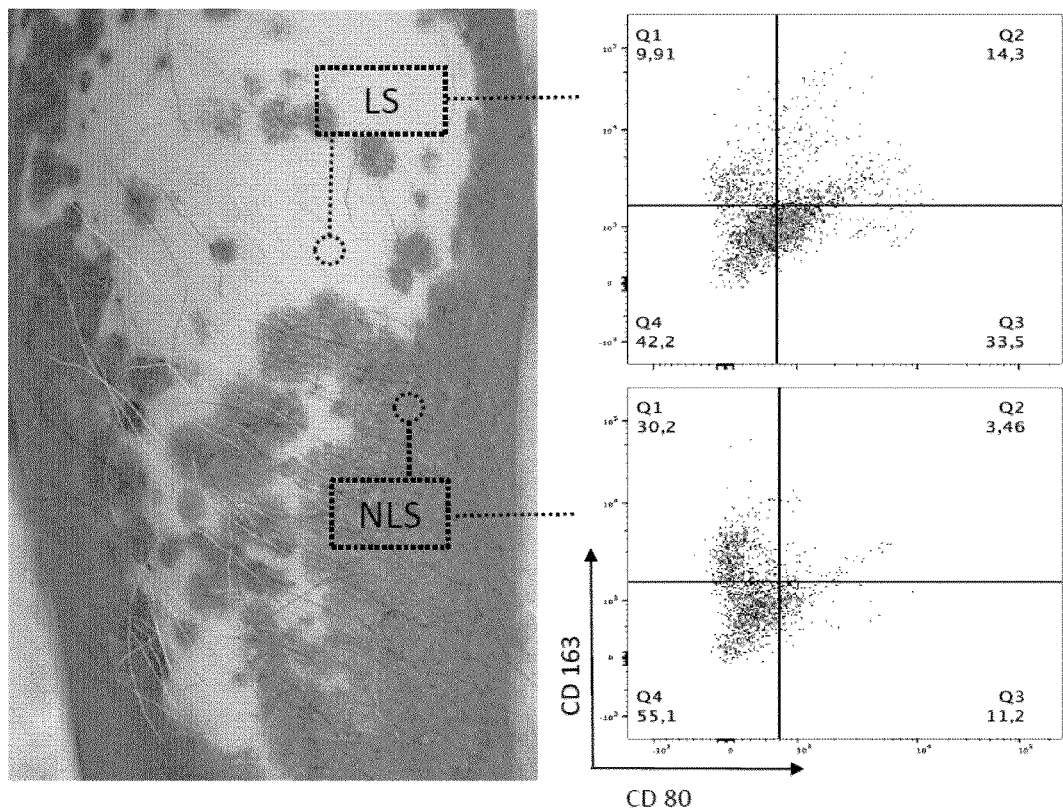
FIG. 3 shows M1(CD80+) and M2 (CD163+) macrophages in Vitiligo skin biopsies, wherein (A) shows full thickness biopsies (5 mm punch) were obtained from vitiligo patients' non-lesional skin (NS) and lesional skin (LS), and used for cell isolation, after 12 hours of incubation, the cells were labeled with CD11b, CD80 (M1 marker) and CD163 (M2 marker) antibodies and analyzed using a cell sorter; (B) shows the FACS distribution of CD11b+ cells being M1 (Q3) and M2 (Q1) in LS and NLS of a representative vitiligo patient; and (C) shows the averages of M1 and M2 macrophages in NLS and LS from three vitiligo patients are shown.
Figure 3:
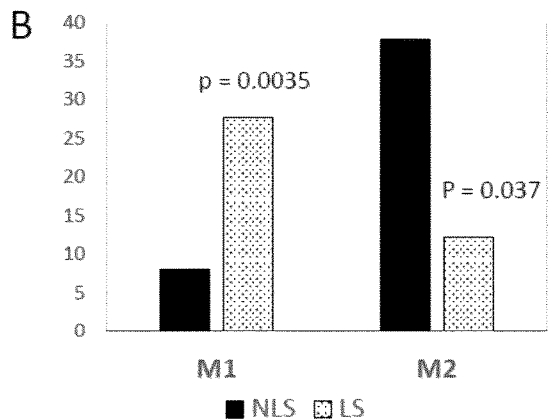
Figure 3:
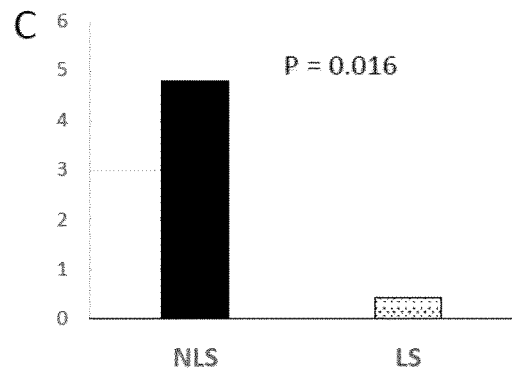
Figure 11:
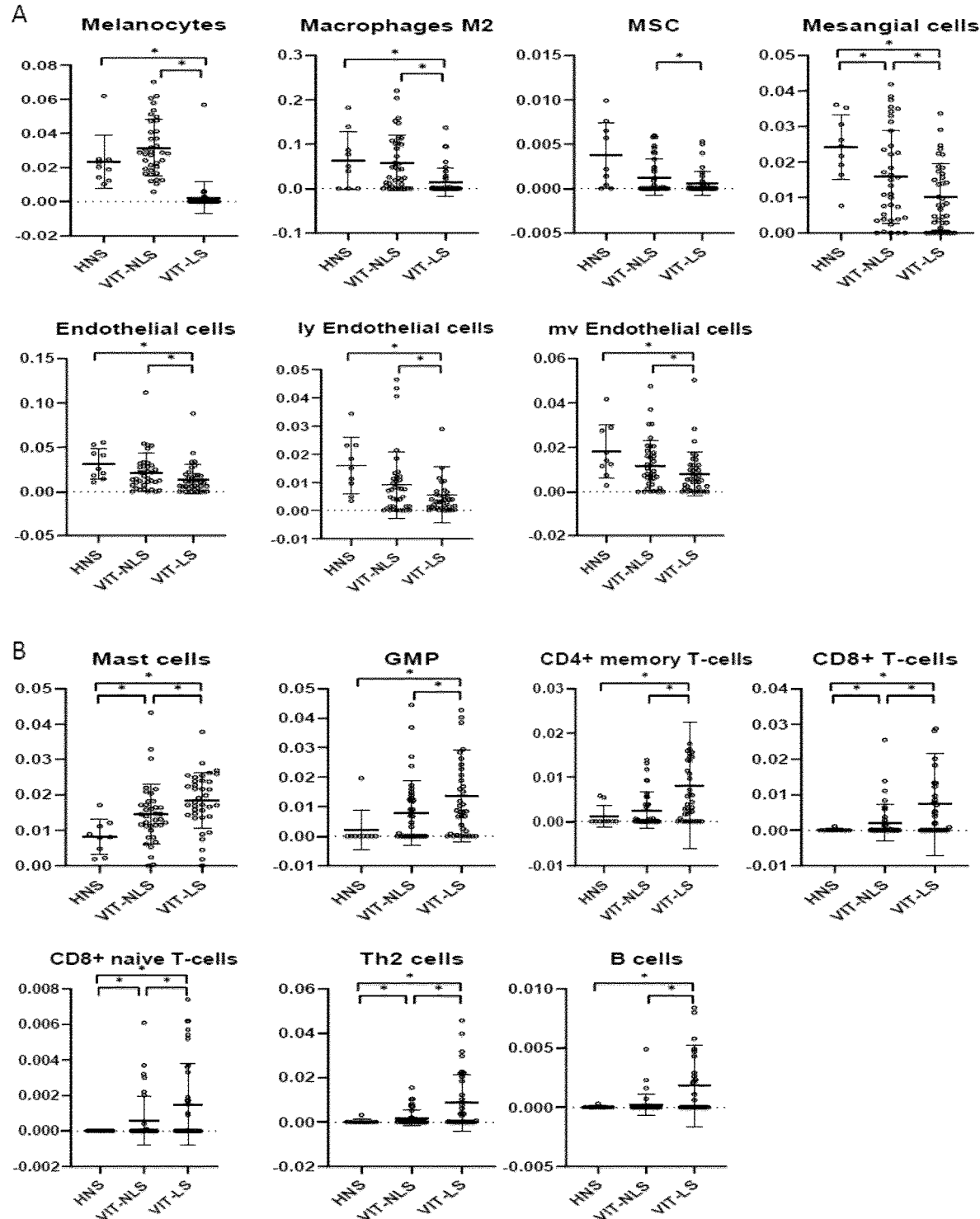
FIG. 11 shows cells that are depleted or enriched in Vitiligo LS as compared to NLS, where cells from vitiligo LS, vitiligo NLS and HNS were analyzed using xCell deconvolution from RNA sequencing analysis; (A) shows cells with depletion in vitiligo LS relative to NLS; while (B) shows cells with enrichment in vitiligo LS relative to NLS. * p<0.05

Example 2: Defective M2 Macrophage Polarization in Human Vitiligo Lesional Skin by Flow Cytometry Since vitiligo lesional skin showed specific depletion of M2 macrophages in the in silico cell profiling analysis (FIGS. 1, 2, and 11), further experiments were performed to verify this discovery. Fresh skin biopsies were obtained from the lesional and nonlesional skin of patients with vitiligo, and used for cell isolation using protocol of R. Clark et al.[54, 55]. Flow cytometry was performed on CD11b+ cells with monoclonal antibodies against CD80 (M1 marker) and CD163 (M2 marker). As shown in FIG. 3A, the CD163+ cells were significantly reduced in vitiligo lesional skin (LS) compared with non-lesional skin (NLS). While M2 macrophages accounted for 37.3% CD11b+ cells on average in the non-lesional skin, they were reduced to 13% in the lesional skin (p=0.037). The M1 macrophages showed the opposite changes, being enriched in vitiligo lesional skin compared with non-lesional skin (p=0.0035) (FIG. 3B). Thus, there is a significant reduction of M2/M1 ratio in vitiligo lesional skin (0.5) as compared with nonlesional skin (4.7, p<0.016), confirming that M2 polarization was defective in vitiligo lesional skin (FIG. 3C).

Figure 4:
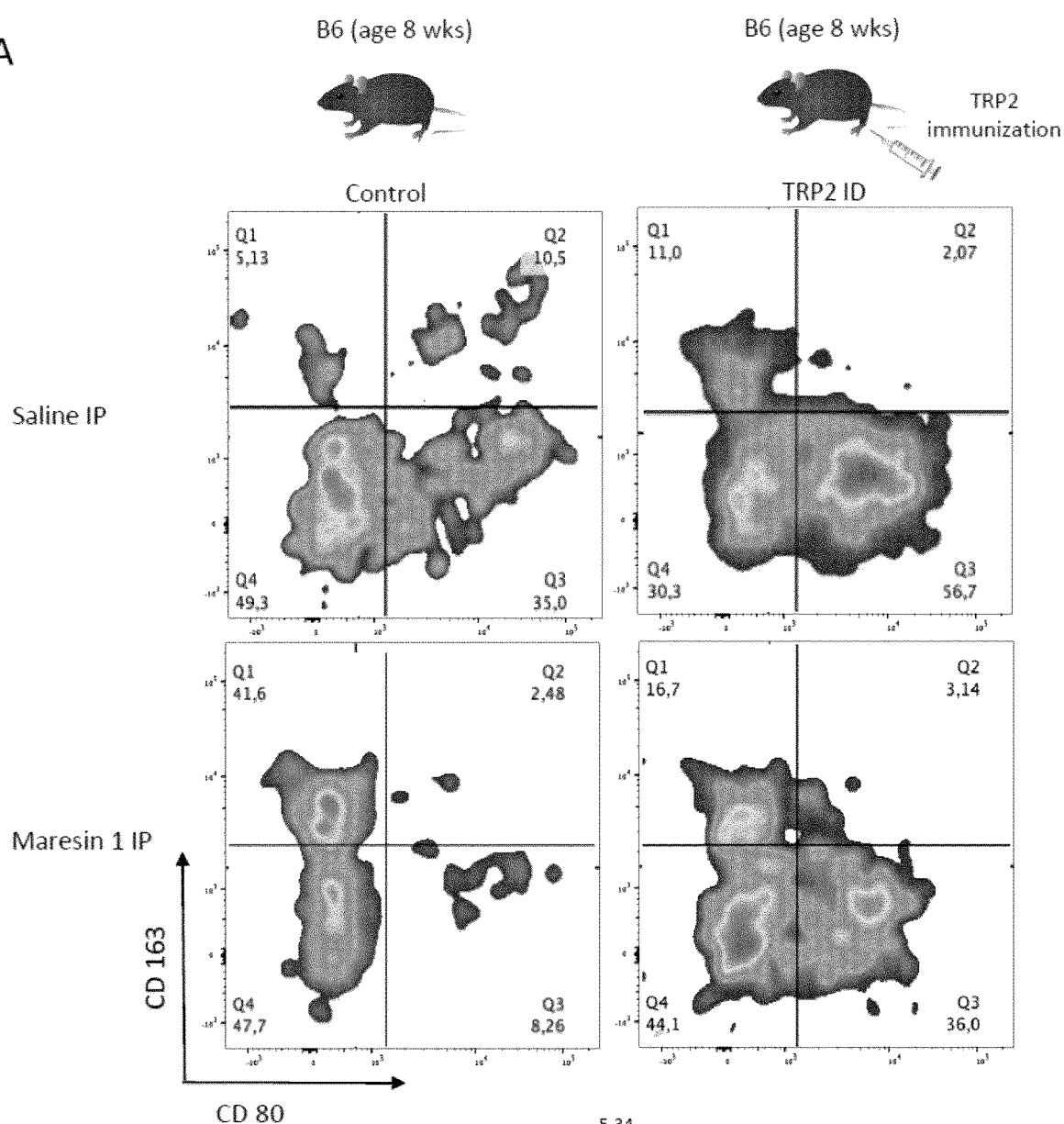
FIG. 4 shows skin resident M2 macrophages in B6 vitiligo mouse model with or without maresin 1 treatment, where the B6 mice were pretreated with either maresin 1 (800 ng/mouse by intraperitoneal injections (IP)) or saline IP daily for three days three times, followed by immunization with TRP2 peptide in an adjuvant containing LPS and CpG by intradermal injections (ID); and forty eight hours after the injection, the mice were euthanized and the skin from the injection site was harvested for cell isolation and flow cytometry using monoclonal antibodies to CD80 (M1 marker) and CD163 (M2 marker), with M2/M1 ratios calculated based on CD163+ cells/CD80+ cells.

Example 3: Decreased M2 Macrophage Polarization in the Skin of B6 Mice Induced to Develop Vitiligo by Immunization Using a Melanocyte-Specific Antigen To test if M2 macrophage depletion is also present in animal models of vitiligo, we employed a well-established B6 vitiligo mouse model that is mediated by melanocyte-specific cytotoxic CD8+ T cells[53, 56]. This model involves intradermal immunization of the B6 (black) mouse with a melanocyte-specific antigen TRP-2 in an adjuvant that contains LPS and CpG, which elicits a robust acute immune response at the immunization site (redness and swelling), that is then followed by the development of white patches of hair (vitiligo) in about 6 weeks. To test if this process involves M2 macrophage depletion, we obtained skin biopsies from the immunization sites 48 hours after immunization (when the immunization response is at its peak), and used flow cytometry to measure M2/M1 ratio. As shown in FIG. 4, TRP2 immunization resulted in a significant reduction of M2 polarization, with M2/M1 ratio decreasing from 0.44 to 0.21.

Example 4: Maresin 1 Treatment of B6 Mice Enhanced Skin M2 Macrophage Polarization and Reduced Melanocyte Depletion Upon Vitiligo Induction M2 macrophages are known to secrete a potent soluble functional mediator, maresin 1, which not only mediates the diverse functions of M2 macrophages, but also stimulates M2 macrophage polarization in an autocrine feedback loop[37]. To test if M2 macrophage depletion contributes to melanocyte depletion in B6 mouse vitiligo model, we pretreated the mice with maresin 1 IP prior to TRP2 immunization. As shown in FIG. 4, maresin 1 treatment dramatically enriched M2 macrophages at the TRP2 immunization site, restoring the post-immunization M2/M1 ratio to a level above the pre-immunization state.

After immunization, the mice continued to receive maresin 1 or saline IP treatments three times per week for 8 weeks (FIG. 5A). The mice were observed weekly by visual inspection and photography for development of vitiligo at the immunization site (FIG. 5B). To quantify the severity of vitiligo, a visual scoring template (FIG. 5C) was used, and the averages of depigmentation scores for each group were plotted according the time of observation. There was a significant reduction of vitiligo development in the maresin 1 treated group compared with sham treated mice (FIG. 5D).

Example 5: Maresin 1's Inhibitory Effects on Melanocyte Depletion was Correlated with Immure Resolution Effects Since maresin 1 has strong pro-resolution effects on inflammation and immune responses, we evaluated the correlation between peak immunization response and the level of depigmentation in maresin 1 treated mice. As shown in FIG. 5E, maresin 1 treatment significantly reduced the immunization response. Further, there was a significant correlation between immunization response score and vitiligo depigmentation area score (FIG. 5F, p<0.0001), suggesting that maresin 1 hasvitiligo-inhibitive effects and that those effects could in part could be attributed to its ability to suppress and resolve melanocyte-specific immune response induced by immunization with TRP-2 peptide.

Example 6: B6 Mouse as a Model of Canities

To evaluate if maresin 1 also could attenuate immune independent melanocyte depletion, we performed additional studies in B6 mouse canities model. Canities is a natural phenomenon that develops in humans and other mammals with advancing age. Recent studies demonstrated that canities development in mice is not the result of immune activation, but a result of aging-associated melanocyte decline due to exhaustion of melanocyte stem cells[57,58]. In our vitiligo studies using B6 black mice, we noted that non-immunized B6 mice naturally developed canities starting at about 3 months of age with approximately 30% mice showing scattered white hairs that were mixed with normal pigmented black hairs in a diffused distribution throughout the hair covered skin, and that there was a significant association between canities development and experience of mental stress caused by sharing cage with a barbering aggressive mouse (FIG. 12), consistent with the previous observation that sympathetic nervous hyperactivation rather than immune activation causes premature canities[57, 58].

Figure 6:
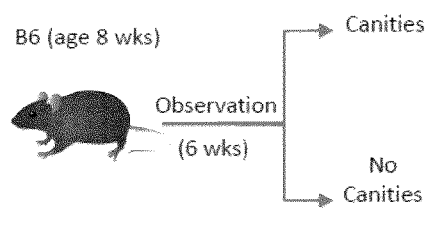
FIG. 6 shows the effect of maresin 1 on melanocyte depletion in B6 mouse canities model; (A) shows B6 mice (aged 8 weeks) were kept in standard conditions for 6 weeks, when approximately 40% of the mice develop grey hair (canities); (B) shows mice that were sacrificed and the venous blood was collected and used for serum preparation and the concentrations of maresin 1 in the serum for mice with canities and mice without canities were determined using ELISA; (C) shows B6 mice (aged 8 weeks) divided into two groups (N=20 per group), where one group received maresin 1 by IP injections three times per week at 800 ng/mouse for an additional 6 weeks and the other group received IP injection of normal saline, while the mice were observed weekly with visual inspection, digital photography; (D) shows and body weight measurement; (E) shows the percentage of mice developing canities in each group was plotted over time; while (F) shows the statistical significance measured by Log Rank test.
Figure 6:
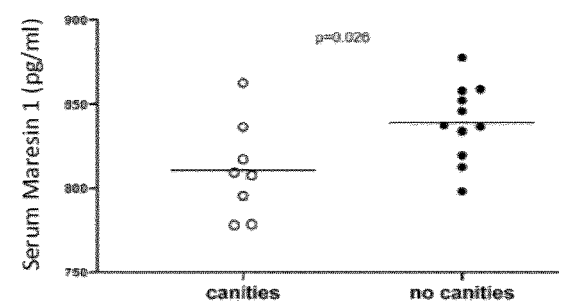
Figure 6:
Figure 6:
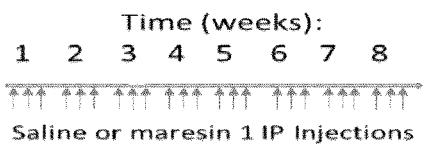
Figure 6:
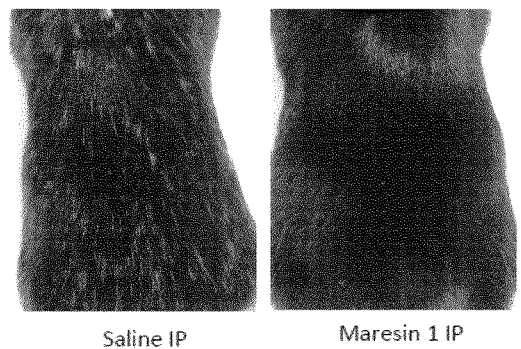
Figure 6:
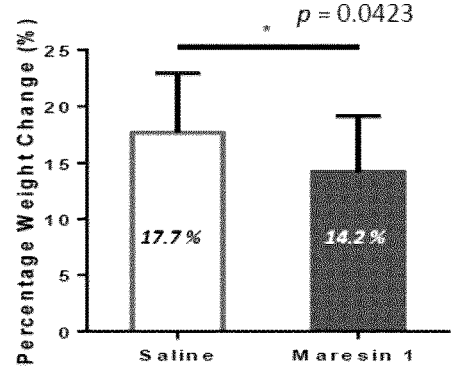
Figure 6:
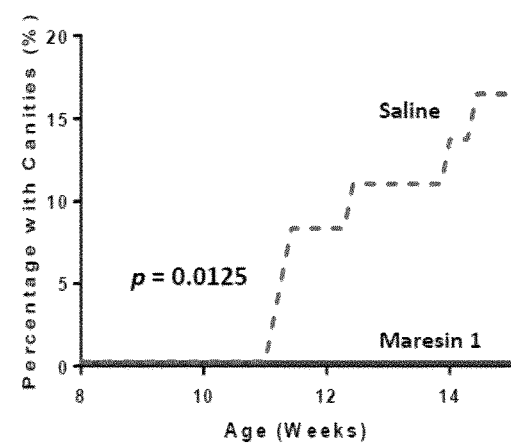

Example 7: Canities Development in B6 Mice was Correlated with Decreased M2 Macrophage Function Since white hair development due to immune-induced melanocyte depletion in B6 vitiligo mice was correlated with suppressed M2 macrophage polarization, we wondered if non-immune mediated melanocyte depletion in canities was also correlated with reduced M2 macrophage function. To test this, we measured serum maresin 1 as a surrogate marker of M2 macrophages, as maresin 1 is mainly produced by M2 macrophages[36, 37] As shown in FIGS. 6A and 6B, the serum level of maresin 1 was significantly lower in mice that developed canites as compared with the age and sex matched B6 mice without canities (p=0.026).

Example 8: Augmentation of M2 Macrophage Function with Maresin 1 Prevented Canities Development as Well as Aging-Associated Weight Gain in B6 Mice To test if maresin 1 reduction contributes to canities development, we divided B6 mice into two groups (FIG.

6C), one receiving 800 ng maresin 1 IP injections three times a week for 8 weeks. The other group receiving saline IP injections. The mice were examined weekly by visual inspection and photography to document hair color, general appearance, and behavior, and by gravimetry to assess aging associated weight gain. As shown in FIG. 4D, meresin 1 treatment significantly enriched M2 macrophages in the skin of B6 mice, increasing M2/M1 ration from 0.44 to 5.34. The maresin 1 treated mice maintained healthier body weight, with a significantly lower aging associated weight gain compared with saline treated control mice (14.2% weight gain vs 17.7% weight gain, p=0.0423) (FIG. 6E), suggesting maresin 1 may have a global antiaging effects in B6 mice. Further, as shown in FIG. 6F, in the saline treated control group 15% of the mice developed canities by 15 weeks of age. In the maresin 1 treatment group, canities development was completely blocked (p<0.0125, Log Rank Test).

Example 9: Maresin 1 Prevents Depletion of Cultured Epidermal Melanocytes Due to Physiological Distress In Vitro It is unknown how maresin 1 treatment prevents melanocyte depletion in vitiligo and canities. Theoretically, this effect could be due to indirect effects, such as through suppressing immune mediated cytotoxicity against the melanocytes, or through direct protective effects on the melanocytes or melanocyte precursors/stem cells. The fact that the reduction of vitiligo depigmentation effects of maresin 1 were tightly correlated with its ability to decrease immunization reaction triggered by TRP2 immunization suggests that immune resolution could explain at least in part the mechanism used by maresin 1 to prevent melanocyte depletion in vitiligo. However, the fact that maresin 1 could also prevent immune-independent melanocyte depletion caused by stem cell exhaustion in canities suggests that maresin 1 might also have a direct protective role on the melanocytes or their precursors.

Figure 7:
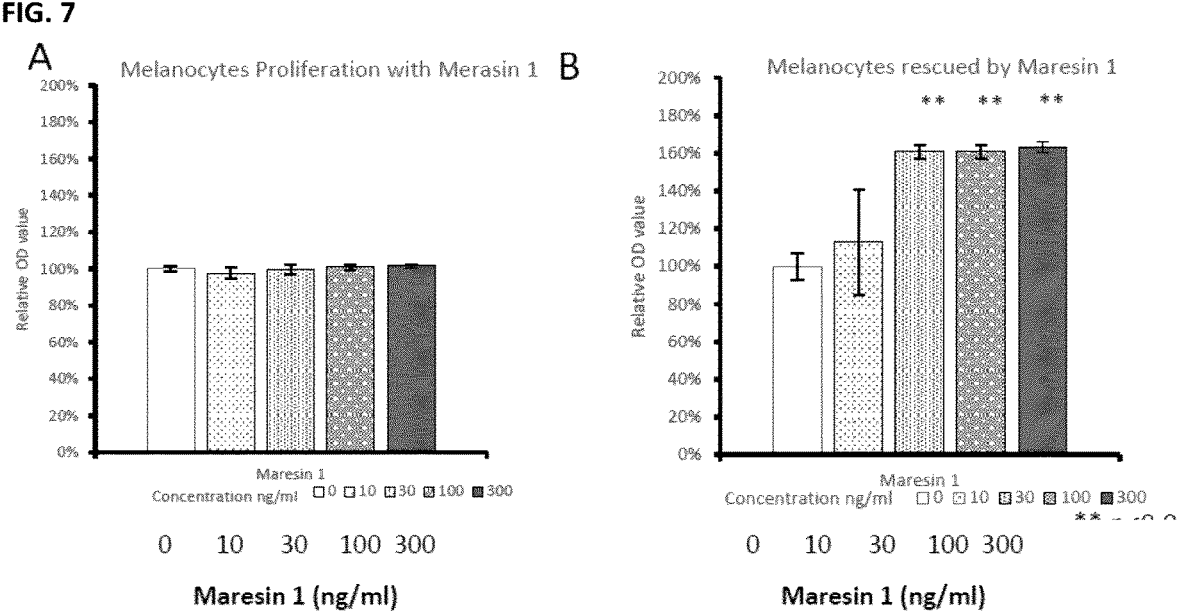
FIG. 7 shows maresin 1 promotes melanocyte survival in culture, wherein (A) shows primary human epidermal melanocytes ($1 \times 10^6$) from neonatal foreskin were obtained from ATCC, and cultured in complete melanocyte growth medium (MGM) and in the presence of 0 to 300 ng/ml of maresin 1 for three days, where the total number of cells in each well was estimated using Clear Titer Blue (CBD) assay and the results are expressed as % of control (0 ng maresin/ml); and (B) shows the assay was done in the same fashion as in (A) except that the growth factor supplement was withdrawn, which triggers melanocyte depletion in the absence of maresin 1 treatment and in the presence of maresin 1 (10 to 300 ng/ml), there was a significant reduction of melanocyte depletion, as reflected by the significant increase of surviving melanocytes. ** p<0.01.

To test this possibility, we cultured primary human epidermal melanocytes (and precursors) isolated from neonatal foreskin. Under normal culture conditions, the melanocytes increase in number as a result of proliferation or differentiation from proliferating precursors in the culture. However, under physiological distress (withdrawal of growth factors in the culture medium), there is a significant depletion in the surviving melanocytes after three days in culture. As shown in FIG. 7, maresin 1 treatment had a significant protective effect on the melanocytes, markedly reducing melanocyte depletion caused by growth factor withdrawal. Since there were no immune cells present in the assay, the anti-depletion effects of maresin 1 on melanocytes appear to be independent of its immune-resolution effects. Instead, maresin 1 likely acts directly on melanocytes or their precursors to prevent melanocyte depletion due to growth factor withdrawal.

Example 10: Melanocyte-Protective Effects of Other Specialized Pro-Resolving Mediators (SPMs)

Figure 8:
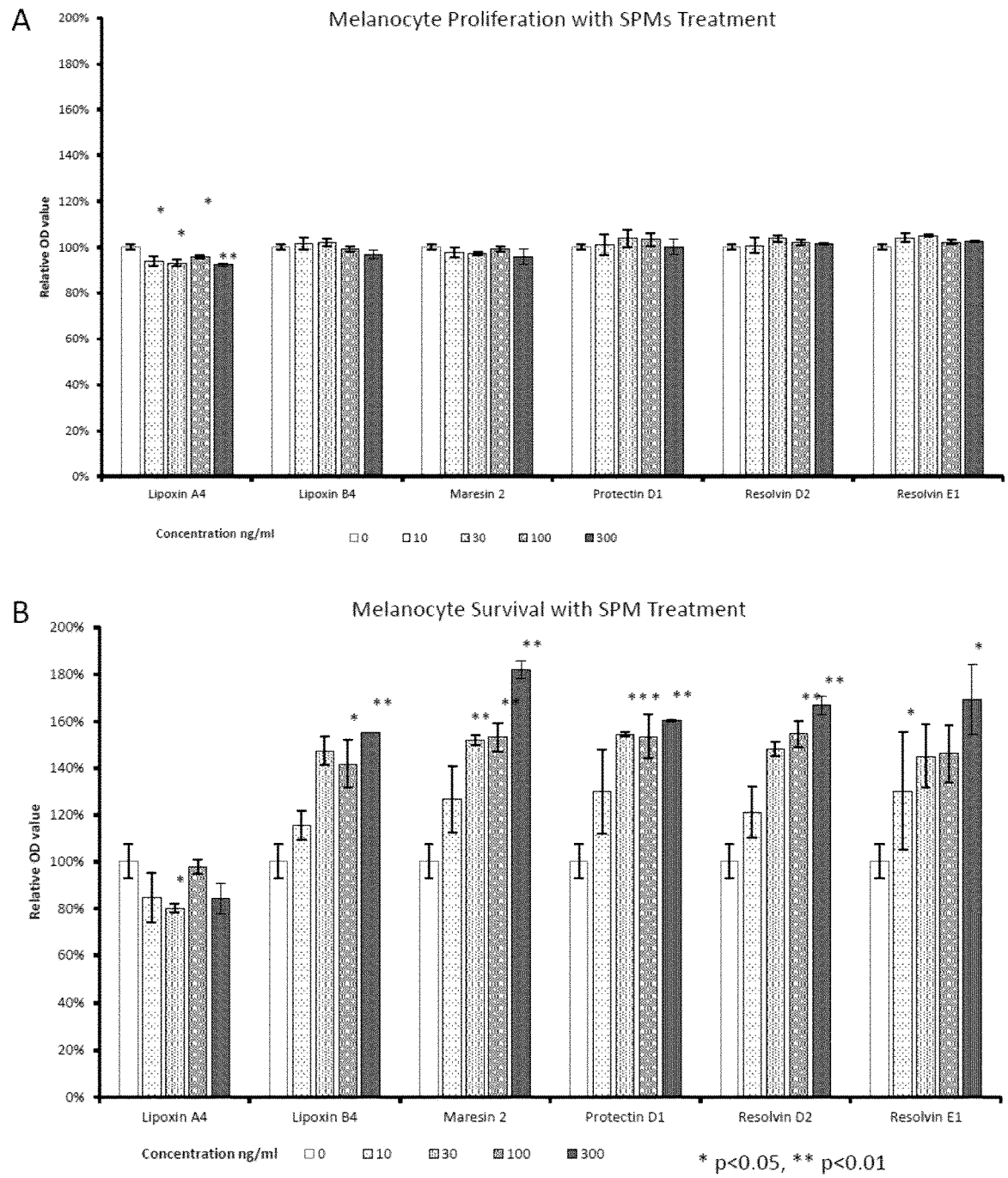
FIG. 8 shows the effects of various specialized pro-resolving mediators on depletion of cultured melanocytes in vitro, wherein (A) shows the effects of SPMs (0 to 300 ng/ml) on growth of primary epidermal melanocytes in complete melanocyte growth medium; and (B) shows he same as (A), except that the growth factor supplements were withdrawn from the base melanocyte growth medium. * p<0.05; ** p<0.01 (t test, each concentration compared with the no treatment control (0 ng/ml))

Maresin 1 is a member of a growing family of SPMs, which are lipid derived mediators capable of resolving immune response and inflammation. There are four main groups of SPMs, the maresins, protectins, resolvins (E and D series), and lipoxins. To test if the protective effect of maresin 1 on melanocytes is present in other SPMs, we performed in vitro melanocyte proliferation and survival assays using mediators representing various SPM groups (i.e. maresin 1; maresin 2; lipoxin A4; lipoxin B4; protectin D1; resolvin D2; and resolvin E1). As shown in FIG. 8, most species of SPMs have robust concentration-dependent pro-survival effects directly on the melanocytes in vitro, with lipoxin A4 being the only exception. Lipoxin A4 not only did not have pro-survival effects on the melanocytes, it significantly decreased melanocyte survival in a concentration independent fashion (FIG. 8).

Example 11: Topical Maresin 1 Leads to Repigmentation of Vitiligo Patches Refractory to Topical Anti-Inflammatory Therapies Topical maresin 1 was tested on a 38 year old Asian man with a 5 year and 3 month history of developing two white patches on the dorsal right hand and one white macule on the right mid abdomen. The white skin patched were first noted in the early summer 5 years ago, and had not changed significantly in size. There were no signs of inflammation such as redness, or presence of scales. There were no symptoms such as itchiness or pain. The subject had been using topical mometasone fumarate 0.1% cream BID for the abdominal macule, and clobetasol 0.05% cream OD for the two patches on the right hand for the past 12 months and did not notice any change in the size of the white areas.

The subject had been healthy, with no history or diagnosis of thyroid diseases, cutaneous lupus or other chronic inflammatory diseases. The subject reported no exposure to chemicals such as benzene or phenol, or used any known skin depigmentation drugs such as hydroquinone or monobenzoether of hydroquinone.

On examination, the subject appeared to be well. Complete skin examination was performed. The entire skin appeared to be normal aside from three lesions of depigmentation: (1) a 1.5×1.2 cm white patch on the mid right abdomen; (2) a 1.3×1.0 cm white patch on the dorsum of right third metacarpal head; and (3) a 1.0×0.8 cm sized white macule on the dorsum of right $4^{th}$ metacarpal head.

Since the subject did not respond to the standard anti-inflammatory medications for 12 months, the subject was looking for other treatment options, and decided to try an ethanol solution containing 0.01% maresin 1 twice daily. The subject did no notice any adverse events such as irritation, itchiness or redness. By the end of three months, the subject noted significant repigmentation starting from peripheral margin and moving centrally. The areas of the three depigmented lesions were decreased by 11.7% (13.6%, 10.5% and 11.1%, for the three lesions, respectively).

Discussion

Despite sharing the loss of melanin pigmentation, vitiligo and canities differ significantly in reported pathogenic mechanisms based on available literature. Melanocyte depletion in vitiligo is mainly mediated by immune destruction of differentiated melanocytes in the epidermis and hair follicles, whereas the melanocyte depletion in canities is the result of exhaustion of melanocyte stem cells that is independent of immune response. Our results collectively point to a previously unknown shared mechanism contributing to melanocyte depletion in vitiligo as well as in canities (i.e. through a deficiency in M2 macrophages or their functional mediator maresin 1 or other suitable SPM).

Our results demonstrated that M2 macrophages, through production of functional mediator maresin 1 or other suitable SPM, are required to maintain the homeostasis niche for the melanocytes by suppressing immune mediated attacks on melanocytes and by directly promoting survival of the melanocytes or their precursors. M2 macrophage function may maintain melanocyte homeostasis by two complementary mechanisms. One, being the pro-resolving function of maresin 1 or other suitable SPM keeps the immune cytotoxicity low in the normal microenvironment for the melanocytes and their precursors. Two, being maresin 1 or other suitable SPM pro-survival function on melanocytes or precursors reduces melanocyte death caused by spontaneous aging, or distress induced by sympathetic hyper-activation or withdrawal of growth factors. In contrast, deficiency of M2 function makes the homeostatic niche unfavorable for the melanocytes, leading to melanocyte depletion due to unchecked immune cytotoxicity and inadequate melanocyte protection. Importantly, the homeostatic environment can be modulated by supplementation with exogenous M2 macrophage functional mediator maresin 1. Our experiments demonstrated that maresin 1 dampens immune cytotoxicity to melanocytes induced by TRP2 (FIG. 5A), increases skin-resident M2 polarization under immune activation (FIG. 4), reduces immune mediated melanocyte destruction in vitiligo mouse model (FIG. 5), prevents non-immune-mediated melanocyte depletion in canities mouse model (FIG. 6), and protects melanocytes from death caused by growth factor starvation in vitro (FIG. 7).

There is growing experimental evidence that M2 macrophages are involved in tissue homeostasis in adult stem cell niches[59], and in the adipose tissue, M2-like macrophages form the niche necessary for the adipocyte precursors[60, 61] Given that exhaustion of melanocyte stem cells is the main mechanism of canities pathogenesis[26] [27], our observations of decreased M2 macrophage function (reduced serum maresin 1 levels) in mice with canities (FIG. 6B), and maresin 1 treatment preventing canities development (FIGS. 6D and F), strongly suggest that M2 macrophages also are necessary for maintaining melanocyte homeostasis.

Previous studies showed that melanocyte homeostasis depends on the maintenance of the pool of stems cells, as loss of the stems cells leads to the aging of the hair follicles[62] Maintenance of the niche required by the stem cells in the hair follicles involves a network of molecular signaling events, such as Col17a1[62], wnt/b-catenin signing[63], SCF/kit signaling[64, 65], suppression of oxidative stress[66], and CXCL12[67]. Our results add M2 macrophages as another essential piece in the puzzle of the signaling network required for the maintenance of melanocyte homeostasis niche.

Figure 12:
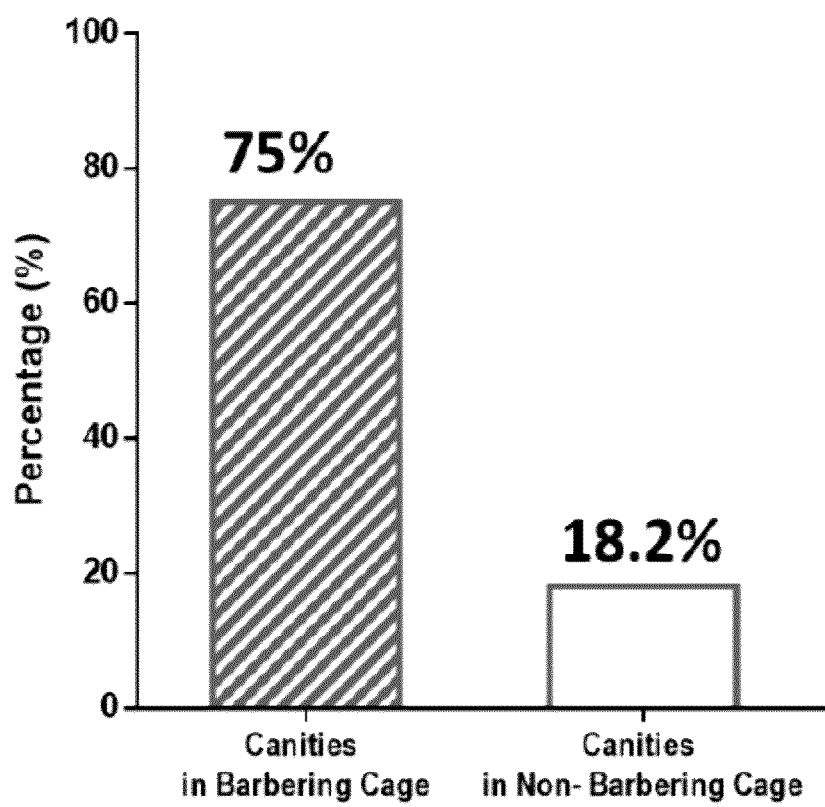
FIG. 12 shows the impact of mental stress on canities development in B6 mice, where B6 mice were housed in standard conditions in cages at a density of 4 mice per cage, the littermates remained unchanged throughout the observation, but in about 40% of the cages, there is a littermate with (barbering) behavior, removing hair by biting the other littermates in the same cage, which can be identified by spotty hair loss and visible bite marks on inspection; the mice were stratified according to presence or absence of a barbering littermate sharing their cages, and the percentage of mice developing canities by week 6 were recorded and showed there was a significant increase in percentage of mice with canities development in mice sharing cages with a barbering mouse. (Chi-sq, p<0.0076)

The studies in murine models by B Zhang et al. showed that hyperactive sympathetic signaling induced by mental stress can lead to exhaustion of melanocyte stem cells resulting in melanocyte depletion in the hair follicles, which is independent of immune response[26] Our results confirmed the strong link between mental stress and development of canities as mice housed in the same cage with an aggressive cage mates had much higher rate of development of canities (FIG. 12). We further demonstrated that melanocyte stem cell exhaustion induced by mental stress could be prevented by treatment with maresin 1 (FIG. 6), thus expanding the scope of physiological functions of M2 macrophages to include defending against psychological or mental distress.

It is not known how maresin 1 or other SPMs function to maintain melanocyte homeostasis and prevent melanocyte depletion due to immune dependent or independent causes is unknown at present. Previous studies showed that maresin 1 can inhibit oxidative stress which has been shown to be important for vitiligo pathogenesis as well as impairment of melanocyte stem cell niche. It is possible that maresin 1 or other suitable SPMs inhibit melanocyte depletion by prevention of oxidative stress. The fact that in in vitro culture of isolated human epidermal melanocytes maresin 1 can significantly increase melanocyte resistance to depletion induced by physiological distress caused by withdrawal of growth supplements suggests that marein 1 or other suitable SPMs can directly act on the melanocytes or their precursors to promote their survival. The mechanism by which this is achieved is unknown at present.

Maresin 1 (macrophage mediator in resolution of inflammation 1) is a small molecule (molecular weight=363) derivative of docosahexaenoic acid (DHA, an omega-3 fatty acid) through 15 lipoxygenase-mediated oxygenation. A member of specialized pro-resolving mediators (SPMs)[68, 69], maresin 1 mediates M2 macrophages' functions in resolution of inflammation, would healing and tissue regeneration[36]. To date, two types of cellular receptors have been found, G-protein coupled receptor LGR6 and nuclear receptor RORα. RORα is expressed by multiple skin cell types including the melanocytes, whereas LGR6 is not expressed by melanocytes. Further studies are needed to investigate the mechanism used by maresin 1 and other suitable SPMs to stimulate and protect melanocytes.

Our results offer an explanation to the clinical characteristics of vitiligo that could not be explained fully by melanocyte destruction by autoreactive CD8+ T cells[11-13], resident memory T cells[25] and NK cells[46]. Our data suggest that lack of growth support for melanocyte homeostasis in vitiligo lesional microenvironment may help explain why immune suppressants, such as cyclosporine, methotrexate, and cortical steroids, are generally ineffective in bringing back melanocytes to established vitiligo lesions, especially in locations on hands, feet and genital regions.

Given that maresin 1 can suppress immune response as well as directly stimulate melanocytes or their precursors, therapies based on maresin 1 (or other M2 agonists) may have particular advantages over traditional immune-suppression based therapies in the treatment of vitiligo, especially for lesions that are unresponsive to immune-suppressive therapies. In addition to vitiligo, several other conditions involve loss of melanocytes, including canities, chemical leukoderma and aging associated leukoderma. Our results suggest that maresin 1 and other suitable SPM molecules may be able to treat these conditions as well.

The mechanism leading to M2 deficiency in vitiligo and canities requires further investigation. Aging associated decrease in maresin 1 production has been discovered for skeletal muscles[70]. Therefore, our observation of maresin 1 reduction in canities strengthens the link between declining maresin 1 production (and reduction in M2 function in general) and physiological aging, and raises the possibility that maresin 1, and related molecules, may be a treatment for canities and other manifestations of physiological aging. Indeed, in B6 mice treated with martesin 1, we observed a reduction in canities formation as well as aging-associated weight gain, suggesting that maresin 1 may have a more global anti-aging benefits for the mice. Further experiments are warranted to evaluate maresin 1's effects, if any, on other aspects of aging, including cardiovascular, neural and cognitive functions.

Maresin 1 is a member of a growing family of fatty acid-derived specialized pro-resolving mediators (SPMs), which also include protectins, resolvins (D series and E series), and lipoxins. Maresins, protectins and D series of resolvins are derivatives of an omega-3 fatty acid docosahexaenoic acid (DHA, 22:6(n−3)), while E series of resolvins are derived from another omega-3 fatty acid eicosapentaenoic acid (EPA, 20:5(n−3)). In contrast, lipoxins are derived from an omega-6 fatty acid, linoleic acids (LA, 18:2 (n−6)). LA also gives rise to pro-inflammatory mediators (leukotrienes and prostaglandins). It is of note that in addition to maresin1, protectins and resolvins also have strong pro-survival effects on cultured human epidermal melanocytes, a function not shared by lipoxin A4, which not only did not protect melanocytes from physiological distress, it accelerated melanocyte depletion. Therefore, all the SPMs are not interchangeable in their ability to protect melanocytes or melanocyte precursors, which may have implications in the development of therapies based on SPMs for the treatment of depigmentation diseases or other medical conditions in the future. However, as demonstrated herein maresin 1; maresin 2; lipoxin B4; protectin D1; resolvin D2; and resolvin E1 all show ability to protect melanocytes.

Our study also revealed previously unreported decrease of mesenchymal stem cells (MSC) and multiple types of endothelial cells in vitiligo lesional skin (FIGS. 1 and 2). Skin MSCs are specialized fibroblast-like cells participating in tissue homeostasis. They have been found to maintain the microenvironment of central nervous system by regulating the polarization of macrophages[71], and secret pro-survival mediators such as neuroregulin[72] which can inhibit T cell homing to the skin in vitiligo[73]. In addition, they can serve as precursor cells that give rise to other types of skin cells including melanocytes)[74]. The discovery of decreased endothelial cells in generalized vitiligo lesions is surprising given previous reports of increased angiogenesis in segmental vitiligo lesions although no such increase was observed with generalized vitiligo[75]. Further investigations are needed to understand the pathogenic significance of the observed changes in MSC and endothelial cells.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to an embodiment of the present invention. The invention includes all embodiments and variations substantially as hereinbefore described and with reference to the examples and drawings.

REFERENCES

1. Alikhan A, Felsten L M, Daly M, Petronic-Rosic V. Vitiligo: a comprehensive overview Part I. Introduction, epidemiology, quality of life, diagnosis, differential diagnosis, associations, histopathology, etiology, and work-up. J Am Acad Dermatol. 2011; 65(3):473-91.
2. Linthorst Homan M W, Sprangers M A, de Korte J, Bos J D, van der Veen J P. Characteristics of patients with universal vitiligo and health-related quality of life. Arch Dermatol. 2008; 144(8):1062-4.
3. Linthorst Homan M W, Spuls P I, de Korte J, Bos J D, Sprangers M A, van der Veen J P. The burden of vitiligo: patient characteristics associated with quality of life. J Am Acad Dermatol. 2009; 61(3):411-20.
4. Mattoo S K, Handa S, Kaur I, Gupta N, Malhotra R. Psychiatric morbidity in vitiligo and psoriasis: a comparative study from India. J Dermatol. 2001; 28(8):424-32.
5. Ongenae K, Beelaert L, van Geel N, Naeyaert J M. Psychosocial effects of vitiligo. J Eur Acad Dermatol Venereol. 2006; 20(1):1-8.
6. Picardo M, Dell'Anna M L, Ezzedine K, Hamzavi I, Harris J E, Parsad D, et al. Vitiligo. Nat Rev Dis Primers. 2015; 1:15011.
7. Ezzedine K, Lim H W, Suzuki T, Katayama I, Hamzavi I, Lan C C, et al. Revised classification/nomenclature of vitiligo and related issues: the Vitiligo Global Issues Consensus Conference. Pigment Cell Melanoma Res. 2012; 25(3):E1-13.
8. Tang X F, Zhang Z, Hu D Y, Xu A E, Zhou H S, Sun L D, et al. Association analyses identify three susceptibility Loci for vitiligo in the Chinese Han population. J Invest Dermatol. 2013; 133(2):403-10.
9. Quan C, Ren Y Q, Xiang L H, Sun L D, Xu A E, Gao X H, et al. Genome-wide association study for vitiligo identifies susceptibility loci at 6q27 and the MHC. Nat Genet. 2010; 42(7):614-8.
10. Ren Y, Yang S, Xu S, Gao M, Huang W, Gao T, et al. Genetic variation of promoter sequence modulates XBP1 expression and genetic risk for vitiligo. PLoS Genet. 2009; 5(6): e1000523.
11. Ryan G E, Harris J E, Richmond J M. Resident Memory T Cells in Autoimmune Skin Diseases. Front Immunol. 2021; 12:652191.
12. Katz E L, Harris J E. Translational Research in Vitiligo. Front Immunol. 2021; 12:624517.
13. Frisoli M L, Essien K, Harris J E. Vitiligo: Mechanisms of Pathogenesis and Treatment. Annu Rev Immunol. 2020; 38:621-48.
14. Yu R, Huang Y, Zhang X, Zhou Y. Potential role of neurogenic inflammatory factors in the pathogenesis of vitiligo. J Cutan Med Surg. 2012; 16(4):230-44.
15. Chang H C, Sung C W. Efficacy of combination therapy of narrowband-ultraviolet B phototherapy or excimer laser with topical tacrolimus for vitiligo: An updated systematic review and meta-analysis. Photodermatol Photoimmunol Photomed. 2020.
16. Gauthier Y, Almasi-Nasrabadi M, Cario-Andre M, Pain C, Rakhshan A, Ghalamkarpour F. Tacrolimus (FK506) ointment combined with Nb-UVB could activate both hair follicle (HF) and dermal melanocyte precursors in vitiligo: the first histopathological and clinical study. Arch Dermatol Res. 2020.
17. Arora C J, Rafiq M, Shumack S, Gupta M. The efficacy and safety of tacrolimus as mono- and adjunctive therapy for vitiligo: A systematic review of randomised clinical trials. Australas J Dermatol. 2020; 61(1): e1-e9.
18. Satyanarayan H S, Kanwar A J, Parsad D, Vinay K. Efficacy and tolerability of combined treatment with NB-UVB and topical tacrolimus versus NB-UVB alone in patients with vitiligo vulgaris: a randomized intra-individual open comparative trial. Indian J Dermatol Venereol Leprol. 2013; 79(4):525-7.
19. Nordal E J, Guleng G E, Ronnevig J R. Treatment of vitiligo with narrowband-UVB (TL01) combined with tacrolimus ointment (0.1%) vs. placebo ointment, a randomized right/left double-blind comparative study. J Eur Acad Dermatol Venereol. 2011; 25(12):1440-3.

20. Hossani-Madani A R, Halder R M. Topical treatment and combination approaches for vitiligo: new insights, new developments. G Ital Dermatol Venereol. 2010; 145(1): 57-78.
21. Esfandiarpour I, Ekhlasi A, Farajzadeh S, Shamsadini S. The efficacy of pimecrolimus 1% cream plus narrow-band ultraviolet B in the treatment of vitiligo: a double-blind, placebo-controlled clinical trial. J Dermatolog Treat. 2009; 20(1):14-8.
22. Fai D, Cassano N, Vena G A. Narrow-band UVB phototherapy combined with tacrolimus ointment in vitiligo: a review of 110 patients. J Eur Acad Dermatol Venereol. 2007; 21(7):916-20.
23. Hamzavi I, Jain H, McLean D, Shapiro J, Zeng H, Lui H. Parametric modeling of narrowband UV-B phototherapy for vitiligo using a novel quantitative tool: the Vitiligo Area Scoring Index. Arch Dermatol. 2004; 140(6):677-83.
24. Craiglow B G, King B A. Tofacitinib Citrate for the Treatment of Vitiligo: A Pathogenesis-Directed Therapy. JAMA Dermatol. 2015; 151(10):1110-2.
25. Richmond J M, Strassner J P, Zapata L, Jr., Garg M, Riding R L, Refat M A, et al. Antibody blockade of IL-15 signaling has the potential to durably reverse vitiligo. Sci Transl Med. 2018; 10(450).
26. Zhang B, Ma S, Rachmin I, He M, Baral P, Choi S, et al. Hyperactivation of sympathetic nerves drives depletion of melanocyte stem cells. Nature. 2020; 577(7792): 676-81.
27. Huang S, Rompolas P. The Psychology of Gray Hair. Dev Cell. 2020; 52(5):548-9.
28. Smith J. Vitiligo with Grey Hair. Proc R Soc Med. 1933; 26(8):1019.
29. Ezzedine K, Le Thuaut A, Jouary T, Ballanger F, Taieb A, Bastuji-Garin S. Latent class analysis of a series of 717 patients with vitiligo allows the identification of two clinical subtypes. Pigment Cell Melanoma Res. 2014; 27(1):134-9.
30. Ezzedine K, Diallo A, Leaute-Labreze C, Seneschal J, Boniface K, Cario-Andre M, et al. Pre- vs. post-pubertal onset of vitiligo: multivariate analysis indicates atopic diathesis association in pre-pubertal onset vitiligo. Br J Dermatol. 2012; 167(3):490-5.
31. Cucchi M L, Frattini P, Santagostino G, Preda S, Orecchia G. Catecholamines increase in the urine of non-segmental vitiligo especially during its active phase. Pigment Cell Res. 2003; 16(2):111-6.
32. Tanita K, Fujimura T, Sato Y, Lyu C, Kambayashi Y, Ogata D, et al. Bexarotene Reduces Production of CCL22 From Tumor-Associated Macrophages in Cutaneous T-Cell Lymphoma. Front Oncol. 2019; 9:907.
33. Wu X, Hsu D K, Wang K H, Huang Y, Mendoza L, Zhou Y, et al. IL-10 is overexpressed in human cutaneous T-cell lymphoma and is required for maximal tumor growth in a mouse model. Leuk Lymphoma. 2019; 60(5):1244-52.
34. Wu X, Schulte B C, Zhou Y, Haribhai D, Mackinnon A C, Plaza J A, et al. Depletion of M2-like tumor-associated macrophages delays cutaneous T-cell lymphoma development in vivo. J Invest Dermatol. 2014; 134(11):2814-22.
35. Sugaya M, Miyagaki T, Ohmatsu H, Suga H, Kai H, Kamata M, et al. Association of the numbers of CD163(+) cells in lesional skin and serum levels of soluble CD163 with disease progression of cutaneous T cell lymphoma. J Dermatol Sci. 2012; 68(1):45-51.
36. Serhan C N, Dalli J, Karamnov S, Choi A, Park C K, Xu Z Z, et al. Macrophage proresolving mediator maresin 1 stimulates tissue regeneration and controls pain. FASEB J. 2012; 26(4):1755-65.
37. Serhan C N, Yang R, Martinod K, Kasuga K, Pillai P S, Porter T F, et al. Maresins: novel macrophage mediators with potent antiinflammatory and proresolving actions. J Exp Med. 2009; 206(1):15-23.
38. Wang C W, Yu S H, Fretwurst T, Larsson L, Sugai J V, Oh J, et al. Maresin 1 Promotes Wound Healing and Socket Bone Regeneration for Alveolar Ridge Preservation. J Dent Res. 2020; 99(8):930-7.
39. Hwang S M, Chung G, Kim Y H, Park C K. The Role of Maresins in Inflammatory Pain: Function of Macrophages in Wound Regeneration. Int J Mol Sci. 2019; 20(23).
40. Gao J, Tang C, Tai L W, Ouyang Y, Li N, Hu Z, et al. Pro-resolving mediator maresin 1 ameliorates pain hypersensitivity in a rat spinal nerve ligation model of neuropathic pain. J Pain Res. 2018; 11:1511-9.
41. Albuquerque-Souza E, Schulte F, Chen T, Hardt M, Hasturk H, Van Dyke T E, et al. Maresin-1 and Resolvin E1 Promote Regenerative Properties of Periodontal Ligament Stem Cells Under Inflammatory Conditions. Front Immunol. 2020; 11:585530.
42. Dalli J, Vlasakov I, Riley I R, Rodriguez A R, Spur B W, Petasis N A, et al. Maresin conjugates in tissue regeneration biosynthesis enzymes in human macrophages. Proc Natl Acad Sci USA. 2016; 113(43):12232-7.
43. Le Poole I C, van den Wijngaard R M, Westerhof W, Das P K. Presence of T cells and macrophages in inflammatory vitiligo skin parallels melanocyte disappearance. Am J Pathol. 1996; 148(4):1219-28.
44. Oiso N, Tanemura A, Kotobuki Y, Kimura M, Katayama I, Kawada A. Role of macrophage infiltration in successful repigmentation in a new periphery-spreading vitiligo lesion in a male Japanese patient. J Dermatol. 2013; 40(11):915-8.
45. Yang Q, Zhang G, Su M, Leung G, Lui H, Zhou P, et al. Vitiligo Skin Biomarkers Associated With Favorable Therapeutic Response. Front Immunol. 2021; 12:613031.
46. Yu R, Broady R, Huang Y, Wang Y, Yu J, Gao M, et al. Transcriptome analysis reveals markers of aberrantly activated innate immunity in vitiligo lesional and non-lesional skin. PLoS One. 2012; 7(12): e51040.
47. Aran D. Cell-Type Enrichment Analysis of Bulk Transcriptomes Using xCell. Methods Mol Biol. 2020; 2120: 263-76.
48. Aran D, Hu Z, Butte A J. xCell: digitally portraying the tissue cellular heterogeneity landscape. Genome Biol. 2017; 18(1):220.
49. Zhang J, Wei X, Tang Z, Miao B, Luo Y, Hu X, et al. Elucidating the molecular pathways and immune system transcriptome during ischemia-reperfusion injury in renal transplantation. Int Immunopharmacol. 2020; 81:106246.
50. Tokumaru Y, Oshi M, Katsuta E, Yan L, Satyananda V, Matsuhashi N, et al. KRAS signaling enriched triple negative breast cancer is associated with favorable tumor immune microenvironment and better survival. Am J Cancer Res. 2020; 10(3):897-907.
51. Lefrancois P, Xie P, Gunn S, Gantchev J, Villarreal A M, Sasseville D, et al. In silico analyses of the tumor microenvironment highlight tumoral inflammation, a Th2 cytokine shift and a mesenchymal stem cell-like phenotype in advanced in basal cell carcinomas. J Cell Commun Signal. 2020; 14(2):245-54.

52. Liss M A, Chen Y, Rodriguez R, Pruthi D, Johnson-Pais T, Wang H, et al. Immunogenic Heterogeneity of Renal Cell Carcinoma With Venous Tumor Thrombus. Urology. 2019; 124:168-73.
53. You S, Cho Y H, Byun J S, Shin E C. Melanocyte-specific CD8+ T cells are associated with epidermal depigmentation in a novel mouse model of vitiligo. Clin Exp Immunol. 2013; 174(1):38-44.
54. Clark R A, Kupper T S. IL-15 and dermal fibroblasts induce proliferation of natural regulatory T cells isolated from human skin. Blood. 2007; 109(1):194-202.
55. Clark R A, Chong B F, Mirchandani N, Yamanaka K, Murphy G F, Dowgiert R K, et al. A novel method for the isolation of skin resident T cells from normal and diseased human skin. J Invest Dermatol. 2006; 126(5):1059-70.
56. You S, Choi Y S, Hong S, Shin E C. Priming of autoreactive CD8(+) T cells is inhibited by immunogenic peptides which are competitive for major histocompatibility complex class I binding. Immune Netw. 2013; 13(3):86-93.
57. Zhang Z, Lei M, Xin H, Hu C, Yang T, Xing Y, et al. Wnt/beta-catenin signaling promotes aging-associated hair graying in mice. Oncotarget. 2017; 8(41):69316-27.
58. Tobin D J. Age-related hair pigment loss. Curr Probl Dermatol. 2015; 47:128-38.
59. Manole E, Niculite C, Lambrescu I M, Gaina G, Ioghen O, Ceafalan L C, et al. Macrophages and Stem Cells-Two to Tango for Tissue Repair? Biomolecules. 2021; 11(5).
60. Nawaz A, Tobe K. M2-like macrophages serve as a niche for adipocyte progenitors in adipose tissue. J Diabetes Investig. 2019; 10(6):1394-400.
61. Lee Y H, Thacker R I, Hall B E, Kong R, Granneman J G. Exploring the activated adipogenic niche: interactions of macrophages and adipocyte progenitors. Cell Cycle. 2014; 13(2):184-90.
62. Matsumura H, Mohri Y, Binh N T, Morinaga H, Fukuda M, Ito M, et al. Hair follicle aging is driven by transepidermal elimination of stem cells via COL17A1 proteolysis. Science. 2016; 351(6273): aad4395.
63. Hendaoui I, Tucker R P, Zingg D, Bichet S, Schittny J, Chiquet-Ehrismann R. Tenascin-C is required for normal Wnt/beta-catenin signaling in the whisker follicle stem cell niche. Matrix Biol. 2014; 40:46-53.
64. Qiu W, Yang K, Lei M, Yan H, Tang H, Bai X, et al. SCF/c-kit signaling is required in 12-O-tradecanoylphorbol-13-acetate-induced migration and differentiation of hair follicle melanocytes for epidermal pigmentation. Cell Tissue Res. 2015; 360(2):333-46.
65. Randall V A, Jenner T J, Hibberts N A, De Oliveira 10, Vafaee T. Stem cell factor/c-Kit signalling in normal and androgenetic alopecia hair follicles. J Endocrinol. 2008; 197(1):11-23.
66. Seiberg M. Age-induced hair greying—the multiple effects of oxidative stress. Int J Cosmet Sci. 2013; 35(6): 532-8.
67. Yamada T, Hasegawa S, Hasebe Y, Kawagishi-Hotta M, Arima M, Iwata Y, et al. CXCL12 regulates differentiation of human immature melanocyte precursors as well as their migration. Arch Dermatol Res. 2019; 311(1):55-62.
68. Chiang N, Serhan C N. Specialized pro-resolving mediator network: an update on production and actions. Essays Biochem. 2020; 64(3):443-62.
69. Spite M, Claria J, Serhan C N. Resolvins, specialized proresolving lipid mediators, and their potential roles in metabolic diseases. Cell Metab. 2014; 19(1):21-36.
70. Markworth J F, Brown L A, Lim E, Castor-Macias J A, Larouche J, Macpherson P C D, et al. Metabolipidomic profiling reveals an age-related deficiency of skeletal muscle pro-resolving mediators that contributes to maladaptive tissue remodeling. Aging Cell. 2021; 20(6): e13393.
71. Xu C, Fu F, Li X, Zhang S. Mesenchymal stem cells maintain the microenvironment of central nervous system by regulating the polarization of macrophages/microglia after traumatic brain injury. Int J Neurosci. 2017; 127 (12):1124-35.
72. Bara J J, Turner S, Roberts S, Griffiths G, Benson R, Trivedi J M, et al. High content and high throughput screening to assess the angiogenic and neurogenic actions of mesenchymal stem cells in vitro. Exp Cell Res. 2015; 333(1):93-104.
73. Zhou M N, Zhang Z Q, Wu J L, Lin F Q Fu L F, Wang S Q, et al. Dermal mesenchymal stem cells (DMSCs) inhibit skin-homing CD8+ T cell activity, a determining factor of vitiligo patients' autologous melanocytes transplantation efficiency. PLoS One. 2013; 8(4): e60254.
74. Crigler L, Kazhanie A, Yoon T J, Zakhari J, Anders J, Taylor B, et al. Isolation of a mesenchymal cell population from murine dermis that contains progenitors of multiple cell lineages. FASEB J. 2007; 21(9):2050-63.
75. Aroni K, Voudouris S, Ioannidis E, Grapsa A, Kavantzas N, Patsouris E. Increased angiogenesis and mast cells in the centre compared to the periphery of vitiligo lesions. Arch Dermatol Res. 2010; 302(8):601-7.

What is claimed is:

1. A method of promoting melanocyte growth and/or survival in a subject having age-associated leukoderma, age-associated leukotrichia, dormant vitiligo lesions, chemically induced vitiligo, vitiligo that is non-responsive to inflammatory therapies, or canities, the method comprising administering to the subject one or more specialized pro-resolving mediators (SPMs) or a pharmaceutically acceptable salt, hydrate, or hydrated salt, or its optical isomer, racemate, diastereoisomer or enantiomer thereof, excluding lipoxin A4.

2. The method of claim 1, wherein the SPM is selected from one or more of the following: maresin 1; maresin 2; lipoxin B4; protectin D1; resolvin D2; and resolvin E1.

3. The method of claim 1, wherein the promoting of melanocyte growth and/or survival promotes re-pigmentation in non-inflammatory depigmentation of skin and hair in the subject.

4. The method of claim 1, where the administering reduces or reverses non-inflammatory loss of melanocytes.

5. The method of claim 1, wherein the administering is as part of a combination therapy with phototherapy or an immune-suppressive therapy.

6. The method of claim 1, wherein the administering is as part of a combination therapy with surgical melanocyte grafting therapy.

7. The method of claim 1, wherein the SPM or a pharmaceutically acceptable salt, hydrate, or hydrated salt, or its optical isomer, racemate, diastereoisomer or enantiomer thereof, is maresin 1.

8. The method of claim 1, wherein the subject has age-associated leukoderma.

9. The method of claim 1, wherein the subject has age-associated leukotrichia.

10. The method of claim 1, wherein the subject has dormant vitiligo lesions.

11. The method of claim 1, wherein the subject has chemically induced vitiligo.

12. The method of claim 1, wherein the subject has vitiligo that is non-responsive to inflammatory therapies.

13. The method of claim 1, wherein the subject has canities.

* * * * *